United States Patent

[19] Iida

[11] Patent Number: 6,140,513
[45] Date of Patent: Oct. 31, 2000

[54] COLOR FORMING DYE PRECURSOR, COMPOSITION CONTAINING THE SAME AND COLOR FORMING HEAT-SENSITIVE RECORDING MATERIAL

[75] Inventor: Kazuyuki Iida, Tokyo, Japan

[73] Assignee: Mitsubishi Paper Mills Limited, Tokyo, Japan

[21] Appl. No.: 08/939,003

[22] Filed: Sep. 26, 1997

[30] Foreign Application Priority Data

Sep. 27, 1996 [JP] Japan ................................ 8-256279
Mar. 28, 1997 [JP] Japan ................................ 9-077435
Aug. 29, 1997 [JP] Japan ................................ 9-234573

[51] Int. Cl.$^7$ .................... C07D 311/82; C07D 311/78
[52] U.S. Cl. ........................... 549/223; 549/224
[58] Field of Search ...................... 549/223, 224

[56] References Cited

U.S. PATENT DOCUMENTS

| | | |
|---|---|---|
| 4,602,263 | 7/1986 | Borror et al. . |
| 4,663,518 | 5/1987 | Borror et al. . |
| 4,720,449 | 1/1988 | Borror et al. ............ 430/338 |
| 4,826,976 | 5/1989 | Borror et al. . |
| 5,220,038 | 6/1993 | Nakatsuka et al. ........ 549/223 |
| 5,434,272 | 7/1995 | Corrie et al. ............ 549/223 |

FOREIGN PATENT DOCUMENTS 7-2865 1/1995 Japan .

OTHER PUBLICATIONS

Eda et al, Chemical Abstracts vol. 122 No. 214053, "Prep. of Fluoran Derivs. as Coloring Agents for Thermal or Press.–Sensitive Recording Materials" (1995).

"Chemistry of Functional Dyes—vol. 2", *Proceedings of the Second International Symposium on Chemistry of Functional Dyes*, Kobe, Aug. 23–28, 1992, edited by Yoshida, Z. and Shirota, Y., pp. 748–753.

*Primary Examiner*—John Kight
*Assistant Examiner*—Raymond Covington
*Attorney, Agent, or Firm*—Pillsbury Madison & Sutro LLP

[57] ABSTRACT

Provided is an electron donating dye precursor represented by the following formula (1), (2), (3) or (4) as defined in the specification which each singly develops two colors upon color forming reaction with one kind of an electron accepting color developer depending on change in the heat energy applied. Furthermore, a heat-sensitive recording material comprising a support and a recording layer containing said electron donating dye precursor and an electron accepting color developer is provided. Moreover, a method for heat sensitive recording of multi-color images using said heat-sensitive recording material is provided.

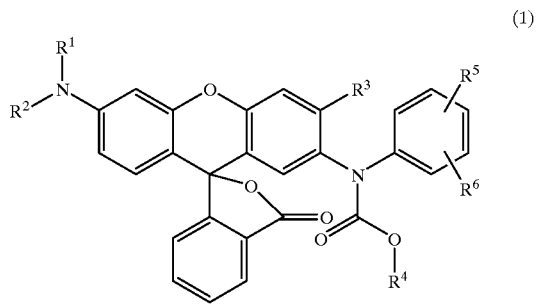

(1)

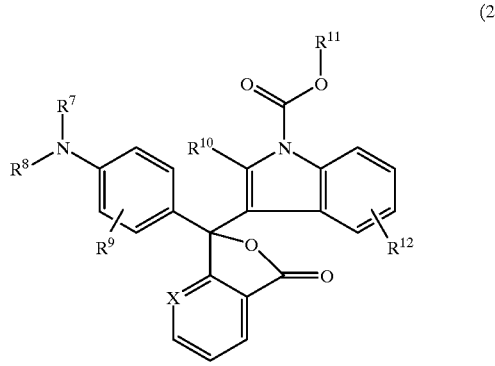

(2)

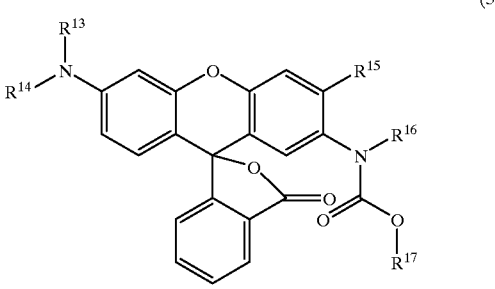

(3)

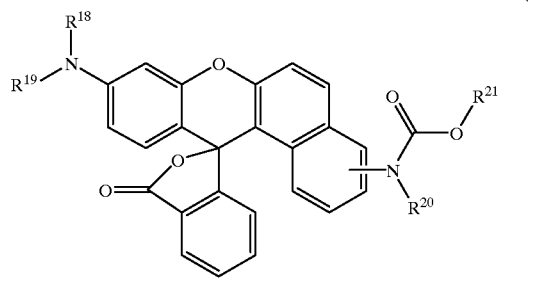

(4)

2 Claims, 11 Drawing Sheets

COLOR FORMING DYE PRECURSOR, COMPOSITION CONTAINING THE SAME AND COLOR FORMING HEAT-SENSITIVE RECORDING MATERIAL

BACKGROUND OF THE INVENTION

The present invention relates to a fluoran color forming dye precursor which alone can form different colors by controlling the heat applied, and a color forming recording material using the same.

Recording materials which utilize color forming reaction of an electron donating dye precursor (hereinafter referred to as "dye precursor") and an electron accepting color developer (hereinafter referred to as "color developer") are well-known as pressure-sensitive recording materials, heat-sensitive recording materials, reversible heat discoloration materials and others.

For example, heat-sensitive recording materials comprise a support and a heat-sensitive recording layer mainly composed of a dye precursor and a color developer provided on the support, and the dye precursor and the color developer instantaneously react with each other upon heating with a thermal head, a thermal pen, a laser beam, etc. to produce recorded images. These are disclosed in JP-B-43-4160, JP-B-45-14039, etc. Since these heat-sensitive recording materials are relatively inexpensive and recording devices are compact and are relatively easy in maintenance, they are used in a wide variety of the fields of not only recording media for facsimile and various computers, but also labels for terminal devices of printers and computers, and automatic vending machines for tickets.

However, with extension of uses of heat-sensitive recording materials, performances and quality required are diversified, and enhancement of sensitivity, increase in fastness of images, reversible recording and multicolor recording are being investigated. Especially, the multicolor recording is wide in the scope of application and a number of recording materials used therefor have been proposed.

Among conventional multicolor recording materials, in the case of two-color heat-sensitive recording materials, colors different at the time of low-temperature heating and high-temperature heating are formed by controlling the heat energy, and the method for multicolor formation can be roughly classified into two methods. According to the first method, color formation of the low-temperature heat-sensitive color forming layer is effected at the time of low-temperature heating and color formation of both the low-temperature heat-sensitive layer and the high-temperature heat-sensitive layer is effected at the time of high-temperature heating to obtain a mixed color. According to the second method, color formation of only the high-temperature heat-sensitive layer is effected at the time of the high-temperature heating by using a color eraser having a color erasing ability in the color forming system where the low-temperature color formation is effected by the low-temperature heating in the first method. Furthermore, in both the methods, two dye precursors forming different colors are separately contained in the low-temperature and high-temperature heat-sensitive layers in order to attain change in color. For example, these are proposed in JP-B-49-69, JP-B-49-4342, JP-B-49-27708, JP-A-49-86543, and JP-A-49-65239.

However, in the case of the first method, the resulting color is a mixed color and the image is indistinct, and in also the second method, the resulting image is considerably deteriorated in storage stability, and, furthermore, an intermediate layer containing the color eraser must generally be provided, which complicates the layer construction of heat-sensitive recording materials. Therefore, two-color heat-sensitive recording materials which are inexpensive and superior in quality cannot be obtained.

On the other hand, as dye precursors which individually can form multicolors, triphenylmethane compounds and indolylphthalide compounds are known in JP-B-60-25276 and "Shikizai Kyokaishi", 64 (7), 425–430 (1991). According to these techniques, two of organic acidic substances such as phenol compounds and organic carboxylic acids and organic basic substances such as guanidine compounds are contained in the same recording layer, and thus it is attempted to realize two-color heat-sensitive recording materials by these different kinds of color developers. Change of color depending on change in heating temperature becomes possible by providing great differences in melting point and dissolving speed of these two color developers. However, since the compounds having just the opposite properties, namely, an acid and a base are used as color developers, the resulting color images are not distinct and further are not utterly practical with regard to image fastness.

Furthermore, as dye precursors capable of being changed in the absorption spectrum utilizing thermal decomposition of carbamate group, U.S. Pat. No. 4,602,263 discloses various triarylmethane dyes, fluoran dyes and thiazine dyes containing thermally unstable carbamate group. However, the object of the invention is formation of full color images, and change of visual absorption spectrum in color forming state of the exemplified thermally decomposable dye precursors is limited to from colored state to colorless state or from colorless state to colored state.

As explained above, there has been known no dye precursor which changes in its chemical structure depending on the change of the heat energy applied and which singly can change clearly from one color to another color by a color forming reaction with a single color developer. Furthermore, color forming recording materials having a single recording layer which forms two colors with one kind of dye precursor have not been practically used as a two-color forming heat-sensitive recording system.

SUMMARY OF THE INVENTION

The present invention provides a dye precursor which changes in its chemical structure depending on the change of the heat energy applied and which singly can form multicolors by a color forming reaction with one kind of color developer. It further provides a heat-sensitive recording material in which the heat-sensitive recording layer comprises a single layer and which can form at least two colors.

The present invention is a color forming dye precursor which changes in its chemical structure with heat energy applied by thermal head, thermal pen, laser beam or the like, whereby it can form multicolors. Specifically, it is a novel fluoran compound represented by the following formula (1), (3) or (4) or a novel indolylphthalide compound represented by the following formula (2). Furthermore, the present invention is a color forming recording composition and a heat-sensitive recording material which uses an electron accepting color developer and at least one of the compounds represented by the formulas (1)–(4) as an electron donating dye precursor.

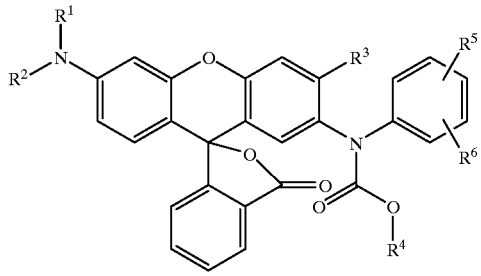

(1)

wherein each of $R^1$ and $R^2$ independently represents an alkyl group, a cycloalkyl group, an alkoxyalkyl group, a tetrahydrofurfuryl group or a substituted or unsubstituted phenyl group, $R^1$ and $R^2$ may link to each other to form a heterocyclic ring together with the nitrogen atom which bonds to $R^1$ and $R^2$; $R^3$ represents a hydrogen atom or a lower alkyl group; $R^4$ represents a tertiary hydrocarbon group or —$(CH_2)_2$—Y in which Y represents an electron attracting group having a positive σ in Hammett's rule; and each of $R^5$ and $R^6$ independently represents a hydrogen atom, a lower alkyl group, a halogen atom, a trifluoromethyl group or an acetyl group.

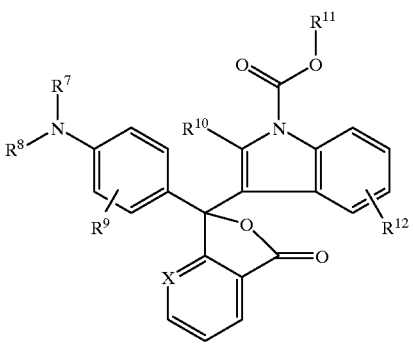

(2)

wherein each of $R^7$ and $R^8$ independently represents an alkyl group, a cycloalkyl group, an alkoxyalkyl group, a tetrahydrofurfuryl group or a substituted or unsubstituted phenyl group, $R^7$ and $R^8$ may link to each other to form a heterocyclic ring together with the nitrogen atom which bonds to $R^7$ and $R^8$; $R^9$ represents a hydrogen atom, a lower alkyl group or a lower alkoxy group; $R^{10}$ represents a hydrogen atom, a lower alkyl group or a substituted or unsubstituted phenyl group; $R^{11}$ represents a tertiary hydrocarbon group or —$(CH_2)_2$—Y in which Y represents an electron attracting group having a positive σ in Hammett's rule; $R^{12}$ represents a hydrogen atom, a lower alkyl group, a halogen atom, a trifluoromethyl group or an acetyl group; and X represents a nitrogen atom or a methine group.

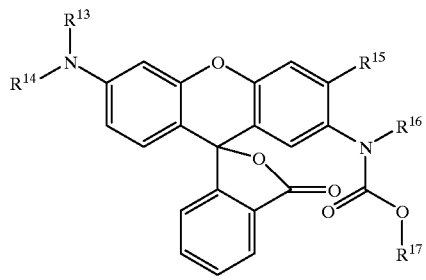

(3)

wherein each of $R^{13}$ and $R^{14}$ independently represents an alkyl group, a cycloalkyl group, an alkoxyalkyl group, a tetrahydrofurfuryl group or a substituted or unsubstituted phenyl group, $R^{13}$ and $R^{14}$ may link to each other to form a heterocyclic ring together with the nitrogen atom which bonds to $R^{13}$ and $R^{14}$; $R^{15}$ represents a hydrogen atom, a lower alkyl group or a lower alkoxy group; $R^{16}$ represents a hydrocarbon group of 1–18 carbon atoms; and $R^{17}$ represents a tertiary hydrocarbon group or —$(CH_2)_2$—Y in which Y represents an electron attracting group having a positive σ in Hammett's rule.

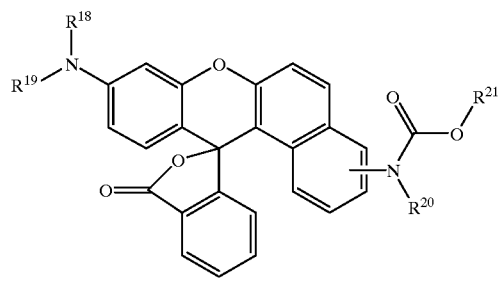

(4)

wherein each of $R^{18}$ and $R^{19}$ independently represents an alkyl group, a cycloalkyl group, an alkoxyalkyl group, a tetrahydrofurfuryl group or a substituted or unsubstituted phenyl group, $R^{18}$ and $R^{19}$ may link to each other to form a heterocyclic ring together with the nitrogen atom which bonds to $R^{18}$ and $R^{19}$; $R^{20}$ represents a hydrocarbon group of 1–18 carbon atoms; $R^{21}$ represents a tertiary hydrocarbon group or —$(CH_2)_2$—Y in which Y represents an electron attracting group having a positive σ in Hammett's rule; and the position of the substituent —N($R^{20}$)—COO$R^{21}$ is 2- or 4-position.

The method for heat sensitive recording of multicolor images according to the present invention comprises applying to the heat-sensitive recording material of the present invention a first heat energy which does not change the chemical structure of the electron donating dye precursor to form a first color image and a second heat energy which changes the chemical structure of the electron donating dye precursor to form a second color image.

DETAILED DESCRIPTION OF THE INVENTION

Figure 1:
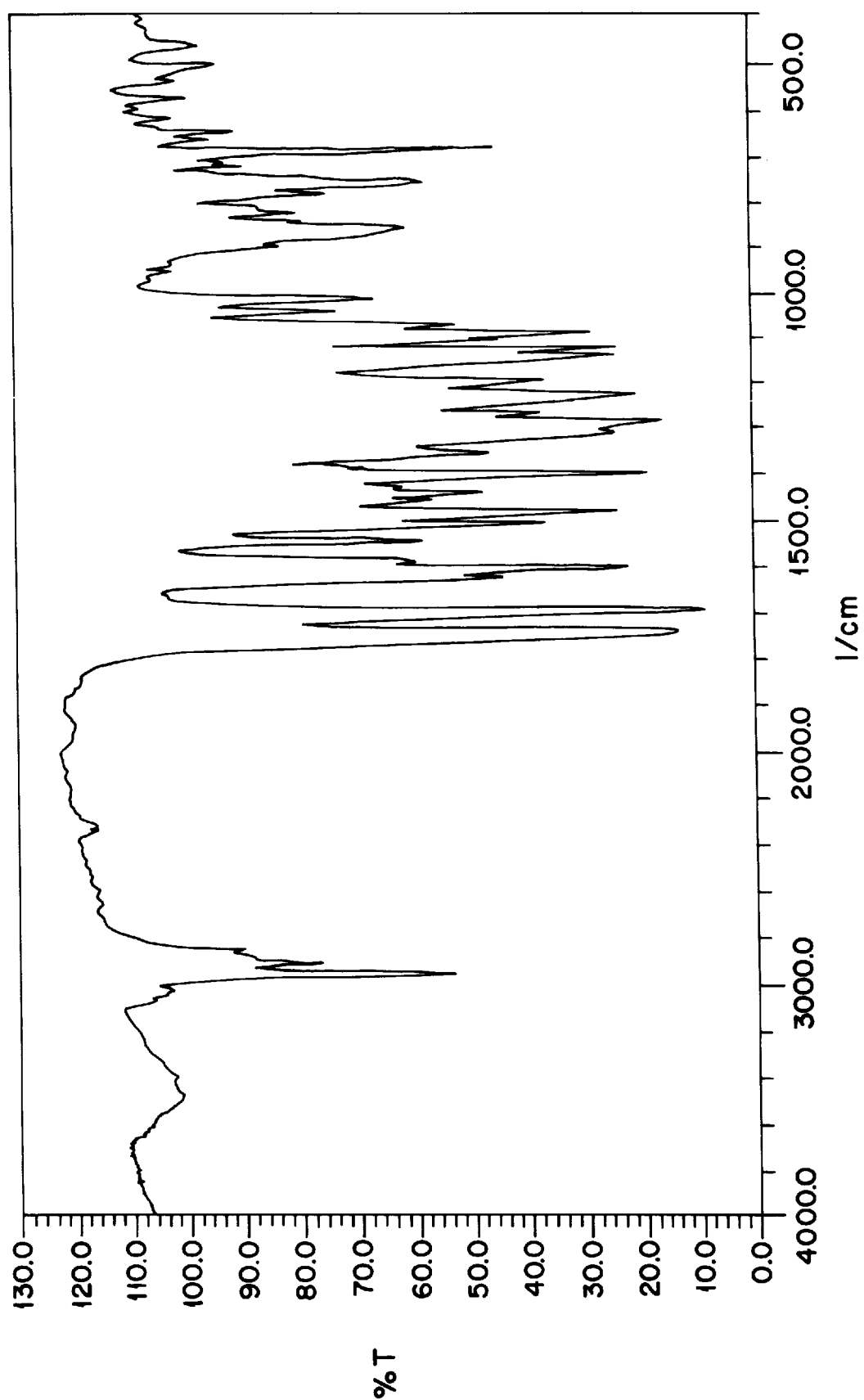
FIG. 1 is an infrared absorption spectrum of Compound 1-2 prepared in Example 1.

The fluoran compound represented by the formula (1) can be prepared in accordance with the following reaction formula A:

Similarly, the compounds represented by the formula (2), (3) and (4) can be prepared by using compound (6), (7) and (8) in place of the starting compound (5) in the reaction formula A, respectively. In this case, $R^4$ in the formulas (9) and (10) in the formula A can be represented as $R^{11}$, $R^{17}$ or $R^{21}$.

$R^1$–$R^{21}$1 in the above formulas (5)–(10) are as defined above. The process for the preparation of the fluoran compound or indolylphthalide compound of the present invention in accordance with the reaction formula A is well known in the field of biochemistry as an urethanation reaction for protecting amino group of amino acid. That is, they can be prepared by reacting the fluoran compound represented by the formula (5), (7) or (8) or the indolylphthalide compound represented by the formula (6) with a dicarbonate ester or a chloroformate ester represented by the formula (9) or (10) in a suitable organic solvent such as tetrahydrofuran or acetonitrile in the presence of a base such as triethylamine or 4-dimethylaminopyridine at room temperature for several hours–several ten hours.

The alkyl group represented by $R^1$ and $R^2$ in the formula (1) is preferably a straight chain or branched chain alkyl group of 1–6 carbon atoms. The cycloalkyl group is preferably that of 5–7 carbon atoms. The alkoxyalkyl group is preferably that of 3–6 carbon atoms. The substituted or unsubstituted phenyl group is preferably a phenyl group

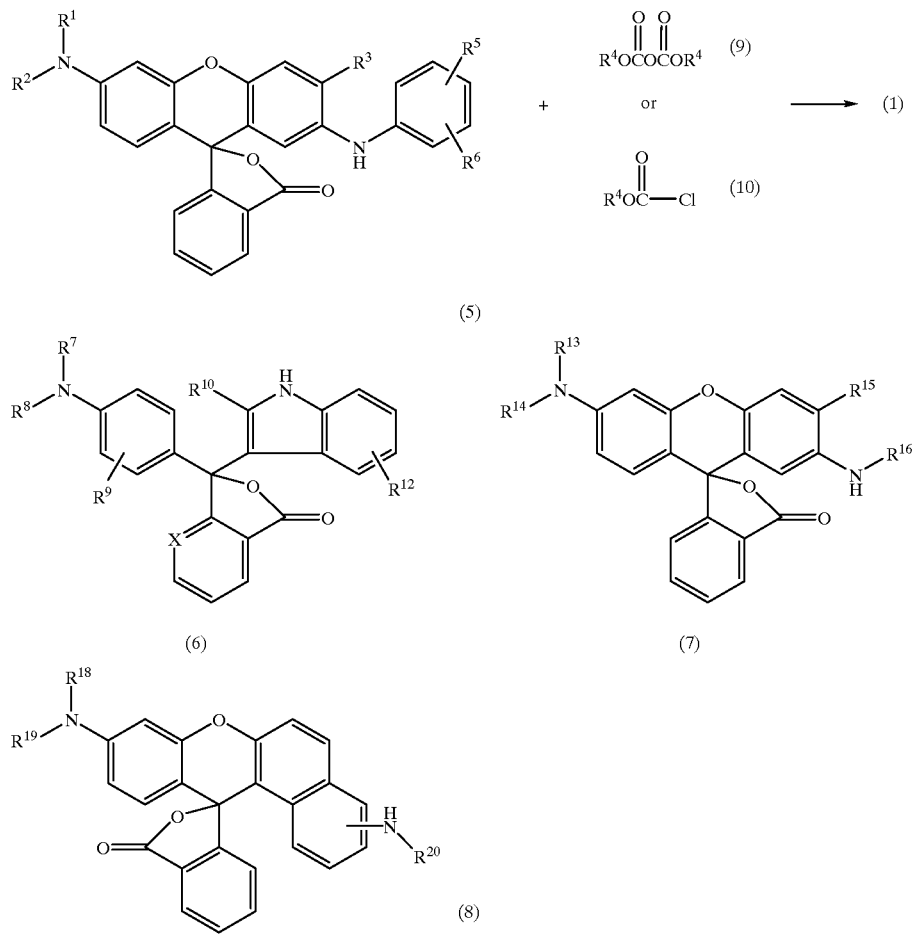

having a lower alkyl group as a substituent or an unsubstituted phenyl group. The heterocyclic ring formed by $R^1$ and $R^2$ together with the nitrogen atom is preferably a pyrrolidino group or a piperidino group. These can also be applied to $R^7$ and $R^8$ in the formula (2), $R^{13}$ and $R^{14}$ in the formula (3), and $R^{18}$ and $R^{19}$ in the formula (4).

The lower alkyl group represented by $R^3$ in the formula (1), $R^{10}$ in the formula (2) and $R^{15}$ in the formula (3) is preferably methyl group or ethyl group, and the lower alkoxy group represented by $R^{15}$ in the formula (3) is preferably methoxy group or ethoxy group.

The tertiary hydrocarbon group represented by $R^4$ in the formula (1), $R^{11}$ in the formula (2), $R^{17}$ in the formula (3) and $R^{21}$ in the formula (4) is most preferably t-butyl group. When $R^4$, $R^{11}$, $R^{17}$ and $R^{21}$ represent —$(CH_2)_2$—Y in which Y represents an electron attracting group having a positive σ in Hammett's rule, the electron attracting group is preferably nitro group, cyano group, carboxy group, formyl group, carbamoyl group, an alkylcarbonyl group such as acetyl group, an arylcarbonyl group, an alkylaminocarbonyl group, an alkylsulfinyl group, an arylsulfinyl group, an alkylsulfonyl group, an arylsulfonyl group, an alkylaminosulfonyl group or the like.

$R^5$ and $R^6$ in the formula (1) and $R^{12}$ in the formula (2) each represent a hydrogen atom, a lower alkyl group, a halogen atom, a trifluoromethyl group or an acetyl group, and the lower alkyl group is preferably methyl group and the halogen atom is preferably chlorine atom.

The color tone formed by the reaction of the fluoran compound of the formula (1) with the general color developer (ring-opening reaction of lactone ring) is basically red irrespective of difference in $R^1$, $R^2$, $R^3$, $R^4$, $R^5$ and $R^6$. When a suitable energy such as high-temperature heating is further applied to this color formed material, the urethane structure in the anilino group on 2-position of the fluoran compound of the formula (1) is decomposed and the fluoran compound represented by the formula (5) is produced, and thus the color tone changes and the second color can be obtained. At this time, the fluoran compound represented by the formula (5) is in the state of the lactone ring being opened due to the reaction with the color developer as in the case of the state of the first color formation. In this case, reddish black, black, blackish green, green, etc. can be obtained by changing the structure of $R^3$, $R^5$ and $R^6$.

Next, the color tone formed by the reaction of indolylphthalide compound of the formula (2) with the general color developer is pink~red~reddish purple depending on the difference in $R^7$, $R^8$, $R^9$, $R^{10}$, $R^{11}$ and $R^{12}$. When a suitable energy such as high-temperature heating is further applied to this color formed material, the urethane structure containing indole hydrogen in the indolylphthalide compound represented by the formula (2) is decomposed to produce the indolylphthalide compound represented by the formula (6), and thus the color tone can be changed. In this case, colors of blue~bluish purple can be obtained by changing the structure of $R^9$, $R^{10}$ and $R^{12}$. Like the above case, the lactone ring in the formulas (2) and (6) is being opened in the state of color formation.

Furthermore, in the case of the fluoran compound of the formula (3), the color formed by the reaction with the general color developer is basically red irrespective of difference in $R^{13}$, $R^{14}$, $R^{15}$, $R^{16}$ and $R^{17}$. When a suitable energy such as high-temperature heating is further applied to this color formed material, the urethane structure in the alkylamino group on 2-position of the fluoran compound represented by the formula (3) is decomposed to produce the fluoran compound represented by the formula (7), and thus the color tone can be changed. In this case, color tones of green~black can be obtained by changing the structure of $R^{15}$ and $R^{16}$. Like the above case, the lactone ring in the formulas (3) and (7) is opened in the state of color formation.

Furthermore, in the case of the fluoran compound of the formula (4), the color formed by the reaction with the general color developer is pink~red depending on the difference in $R^{18}$, $R^{19}$ and $R^{20}$. When a suitable energy such as high-temperature heating is further applied to this color formed material, the urethane structure in the alkylamino group on 2-position or 4-position of the fluoran compound represented by the formula (4) is decomposed to produce the fluoran compound represented by the formula (8), and thus the color tone can be changed, and basically blue color is obtained irrespective of the position of the substituent —$N(R^{20})$—$COOR^{21}$. Like the above case, the lactone ring in the formulas (4) and (8) is opened in the state of color formation.

Nonlimiting examples of the fluoran compounds represented by the formula (1) are enumerated below.

TABLE 1

| Compound Number | Substituents | | | | | |
|---|---|---|---|---|---|---|
| | $R^1$ | $R^2$ | $R^3$ | $R^4$ | $R^5$ | $R^6$ |
| Compound 1-1 | Me | Me | Me | t-Bu | H | H |
| Compound 1-2 | | Et | Me | t-Bu | H | H |
| Compound 1-3 | Bu | Bu | Me | t-Bu | H | H |
| Compound 1-4 | Et | i-Am | Me | t-Bu | H | H |
| Compound 1-5 | Me | cyclohexyl | Me | t-Bu | H | H |
| Compound 1-6 | | —$(CH_2)_4$— | Me | t-Bu | H | H |
| Compound 1-7 | Et | p-Tol | Me | t-Bu | H | H |
| Compound 1-8 | Et | tetrahydrofurfuryl | Me | t-Bu | H | H |

TABLE 1-continued

| Compound Number | R¹ | R² | R³ | R⁴ | R⁵ | R⁶ |
|---|---|---|---|---|---|---|
| Compound 1-9 | Me | —$C_2H_4OCH_3$ | Me | t-Bu | H | H |
| Compound 1-10 | Et | Hex | H | t-Bu | H | H |
| Compound 1-11 | Et | Et | H | t-Bu | m-$CF_3$ | H |
| Compound 1-12 | Et | Et | H | t-Bu | o-Cl | H |
| Compound 1-13 | Bu | Bu | H | t-Bu | H | p-AC |
| Compound 1-14 | Bu | Bu | H | —$C_2H_4\overset{O}{\overset{\|}{C}}CH_3$ | m-$CF_3$ | H |
| Compound 1-15 | —$(CH_2)_4$— | | H | —$C_2H_4CN$ | o-Cl | p-Cl |
| Compound 1-16 | Bu | Bu | H | —$C_2H_4\overset{O}{\overset{\|}{S}}CH_3$ | H | H |
| Compound 1-17 | Bu | Bu | H | —$C_2H_4\overset{O}{\underset{O}{\overset{\|}{\underset{\|}{S}}}}CH_3$ | H | H |

Abbreviations of the substituents in the above table means the following.
Me: Methyl group
Et: Ethyl group
Bu: n-Butyl group
t-Bu: t-Butyl group
i-Am: i-Pentyl group
Hex: n-Hexyl group
p-Tol: p-Methylphenyl group
AC: Acetyl group Nonlimiting examples of the indolylphthalide compounds represented by the formula (2) are enumerated below.

TABLE 2

| Compound Number | R⁷ | R⁸ | R⁹ | R¹⁰ | R¹¹ | R¹² | X |
|---|---|---|---|---|---|---|---|
| Compound 2-1 | Bu | Bu | Me | H | t-Bu | H | N |
| Compound 2-2 | Et | Et | EtO | Me | t-Bu | H | N |
| Compound 2-3 | Et | Et | EtO | Ph | t-Bu | H | N |
| Compound 2-4 | Et | i-Am | MeO | Me | t-Bu | H | CH |
| Compound 2-5 | Me | 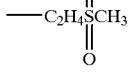 | MeO | Ph | t-Bu | H | N |
| Compound 2-6 | —$(CH_2)_4$— | | Et | Ph | t-Bu | 5-$CH_3$ | CH |
| Compound 2-7 | Et | p-Tol | Me | Ph | t-Bu | H | CH |
| Compound 2-8 | Et | 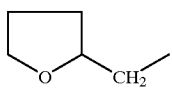 | EtO | Me | t-Bu | H | N |
| Compound 2-9 | Me | —$C_2H_4OCH_3$ | MeO | Me | t-Bu | H | CH |
| Compound 2-10 | Et | Et | EtO | Me | t-Bu | 5-$CF_3$ | N |
| Compound 2-11 | Et | Et | EtO | Me | t-Bu | 5-Cl | N |
| Compound 2-12 | Et | Et | EtO | Me | t-Bu | 5-Ac | N |
| Compound 2-13 | Et | Et | EtO | Me | —$C_2H_4\overset{O}{\overset{\|}{C}}CH_3$ | H | N |

TABLE 2-continued

| Compound Number | Substituents | | | | | | |
|---|---|---|---|---|---|---|---|
| | $R^7$ | $R^8$ | $R^9$ | $R^{10}$ | $R^{11}$ | $R^{12}$ | X |
| Compound 2-14 | Et | Et | EtO | Me | —$C_2H_4CN$ | H | N |
| Compound 2-15 | Et | Et | EtO | Me | —$C_2H_4SCH_3$ (with C=O) | H | N |
| Compound 2-16 | Et | Et | EtO | Me | —$C_2H_4SCH_3$ (with S(=O)$_2$) | H | N |

Abbreviations of the substituents in the above table means the following.
Me: Methyl group
Et: Ethyl group
Bu: n-Butyl group
t-Bu: t-Butyl group
i-Am: i-Pentyl group
p-Tol: p-Methylphenyl group
Ac: Acetyl group
Ph: Phenyl group Nonlimiting examples of the fluoran compounds represented by the formula (3) are enumerated below.

TABLE 3

| Compound Number | Substituents | | | | |
|---|---|---|---|---|---|
| | $R^{13}$ | $R^{14}$ | $R^{15}$ | $R^{16}$ | $R^{17}$ |
| Compound 3-1 | Me | Me | Me | Me | t-Bu |
| Compound 3-2 | Et | Et | H | Et | t-Bu |
| Compound 3-3 | Bu | Bu | Me | Et | t-Bu |
| Compound 3-4 | Et | i-Am | Me | Oct | t-Bu |
| Compound 3-5 | Me | (methylcyclohexyl) | Me | Et | t-Bu |
| Compound 3-6 | —(CH$_2$)$_4$— | | H | Bu | t-Bu |
| Compound 3-7 | Et | p-Tol | Me | Oct | t-Bu |
| Compound 3-8 | Et | (tetrahydrofurfuryl) | Me | Et | t-Bu |
| Compound 3-9 | Me | —$C_2H_4OCH_3$ | Me | Et | t-Bu |
| Compound 3-10 | Et | Hex | H | Et | t-Bu |
| Compound 3-11 | Et | Et | H | Et | t-Bu |
| Compound 3-13 | Bu | Bu | H | Oct | t-Bu |
| Compound 3-14 | Bu | Bu | H | Et | —$C_2H_4CCH_3$ (C=O) |
| Compound 3-15 | —(CH$_2$)$_4$— | | H | Et | —$C_2H_4CN$ |
| Compound 3-16 | Bu | Bu | H | Et | —$C_2H_4SCH_3$ (C=O) |

TABLE 3-continued

| Compound Number | Substituents | | | | |
|---|---|---|---|---|---|
| | $R^{13}$ | $R^{14}$ | $R^{15}$ | $R^{16}$ | $R^{17}$ |
| Compound 3-17 | Bu | Bu | H | Et | $-C_2H_4\underset{\underset{O}{\|}}{\overset{\overset{O}{\|}}{S}}CH_3$ |

Abbreviations of the substituents in the above table means the following.
Me: Methyl group

TABLE 4

| Compound Number | Substituents | | | | Position of $-N(R^{20})-COOR^{21}$ |
|---|---|---|---|---|---|
| | $R^{18}$ | $R^{19}$ | $R^{20}$ | $R^{21}$ | |
| Compound 4-1 | Me | Me | Me | t-Bu | 2— |
| Compound 4-2 | Et | Et | Et | t-Bu | 4— |
| Compound 4-3 | Bu | Bu | Et | t-Bu | 2— |
| Compound 4-4 | Et | i-Am | Oct | t-Bu | 4— |
| Compound 4-5 | Me | cyclohexyl-CH (H) | Et | t-Bu | 2— |
| Compound 4-6 | —(CH₂)₄— | | Bu | t-Bu | 2— |
| Compound 4-7 | Et | p-Tol | Oct | t-Bu | 2— |
| Compound 4-8 | Et | tetrahydrofuryl-CH₂ | Et | t-Bu | 2— |
| Compound 4-9 | Me | —C₂H₄OCH₃ | Et | t-Bu | 4— |
| Compound 4-10 | Et | Hex | Et | t-Bu | 4— |
| Compound 4-11 | Et | Et | Et | t-Bu | 4— |
| Compound 4-13 | Bu | Bu | Oct | t-Bu | 4— |
| Compound 4-14 | Bu | Bu | Et | $-C_2H_4\overset{\overset{O}{\|}}{C}CH_3$ | 4— |
| Compound 4-15 | —(CH₂)₄— | | Et | —C₂H₄CN | 4— |
| Compound 4-16 | Bu | Bu | Et | $-C_2H_4\overset{\overset{O}{\|}}{S}CH_3$ | 4— |
| Compound 4-17 | Bu | Bu | Et | $-C_2H_4\underset{\underset{O}{\|}}{\overset{\overset{O}{\|}}{S}}CH_3$ | 4— |

Et: Ethyl group
Bu: n-Butyl group
t-Bu: t-Butyl group
i-Am: i-Pentyl group
Hex: n-Hexyl group
p-Tol: p-Methylphenyl group
Oct: Octyl group Nonlimiting examples of the fluoran compounds represented by the formula (4) are enumerated below.

Abbreviations of the substituents in the above table mean the following.
Me: Methyl group
Et: Ethyl group
Bu: n-Butyl group
t-Bu: t-Butyl group
i-Am: i-Pentyl group
Hex: n-Hexyl group
p-Tol: p-Methylphenyl group Oct: n-Octyl group The color forming dye precursors of the present invention (the above fluoran compounds and indolylphthalide compounds) can be used each alone or, if necessary, in combination with other dye precursors in the color forming recording materials.

As the dye precursors usable in combination with the color forming dye precursors of the present invention, representative are known dye precursors which are generally used for pressure-sensitive recording materials, heat-sensitive recording materials, etc. Nonlimiting examples of these dye precursors are those enumerated below.

(1) Triarylmethane compounds 3,3-Bis(p-dimethylaminophenyl)-6-dimethylaminophthalide (crystal violet lactone), 3,3-bis(p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl)phthalide, 3-(p-dimethylaminophenyl)-3-(2-phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-5-dimethylaminophthalide, 3,3-bis(2-phenylindol-3-yl)-5-dimethylaminophthalide, 3-p-dimethylaminophenyl-3-(1-methylpyrrol-2-yl)-6-dimethylaminophthalide, etc.

(2) Diphenylmethane compounds 4,4'-Bis(dimethylaminophenyl)benzohydril benzyl ether, N-chlorophenyl leuco Auramine, N-2,4,5-trichlorophenyl leuco Auramine, etc.

(3) Xanthene compounds

Rhodamine B anilinolactam, Rhodamine B-p-chloroanilinolactam, 3-diethylamino-7-dibenzylaminofluoran, 3-diethylamino-7-octylaminofluoran, 3-diethylamino-7-phenylfluoran, 3-diethylamino-7-chlorofluoran, 3-diethylamino-6-chloro-7-methylfluoran, 3-diethylamino-7-(3,4-dichloroanilino)fluoran, 3-diethylamino-7-(2-chloroanilino)fluoran, 3-diethylamino-6-methyl-7-anilinofluoran, 3-(N-ethyl-N-tolyl)amino-6-methyl-7-anilinofluoran, 3-piperidino-6-methyl-7-anilinofluoran, 3-(N-ethyl-N-tolyl)amino-6-methyl-7-phenethylfluoran, 3-diethylamino-7-(4-nitroanilino)fluoran, 3-butylamino-6-methyl-7-anilinofluoran, 3-(N-methyl-N-propyl)amino-6-methyl-7-anilinofluoran, 3-(N-ethyl-N-isoamyl)amino-6-methyl-7-anilinofluoran, 3-(N-methyl-N-cyclohexyl)amino-6-methyl-7-anilinofluoran, 3-(N-ethyl-N-tetrahydrofuryl)amino-6-methyl-7-anilinofluoran, etc.

(4) Thiazine compounds

Benzoyl leuco Methylene Blue, p-nitrobenzoyl leuco Methylene Blue, etc.

(5) Spiro compounds

3-Methylspiro-dinaphthopyran, 3-ethylspiro-dinaphthopyran, 3,3'-dichlorospiro-dinaphthopyran, 3-benzylspiro-dinaphthopyran, 3-methylnaphtho-(3-methoxybenzo)spiropyran, 3-propylspiro-benzopyran, etc.

In the heat-sensitive recording materials in which the color forming dye precursor of the present invention is used, mixing ratio of the dye precursor and the color developer can be optionally varied depending on the kinds thereof, but usually the color developer is used in an amount of preferably about 100–2000% by weight, more preferably 200–1500% by weight based on the dye precursor.

The electron accepting color developers used in the present invention are not limited, but preferred are phenol derivatives, aromatic carboxylic acids or derivatives thereof and metal salts thereof, N,N'-diarylthiourea derivatives, and N-sulfonylurea derivatives. These may be used each alone or in admixture of two or more.

Examples of the phenol derivatives are p-phenylphenol, p-hydroxyacetophenone, 4-hydroxy-4'-methyldiphenyl sulfone, 4-hydroxy-4'-isopropoxydiphenyl sulfone, 4-hydroxy-4'-benzenesulfonyloxydiphenyl sulfone, 1,1-bis(4-hydroxyphenyl)propane, 1,1-bis(4-hydroxyphenyl)pentane, 1,1-bis(4-hydroxyphenyl)hexane, 1,1-bis(4-hydroxyphenyl)cyclohexane, 1,1-bis(4-hydroxyphenyl)cyclododecane, 2,2-bis(4-hydroxyphenyl)propane, 2,2-bis(4-hydroxyphenyl)hexane, 2,2-bis(4-hydroxyphenyl)octane, 1,1-bis(4-hydroxyphenyl)-2-ethylhexane, 2,2-bis(3-chloro-4-hydroxyphenyl)propane, 1,1-bis(4-hydroxyphenyl)-1-phenylethane, 1,3-di-[2-(4-hydroxyphenyl)-2-propyl]benzene, 1,3-di-[2-(3,4-dihydroxyphenyl)-2-propyl]benzene, 1,4-di-[2-(4-hydroxyphenyl)-2-propyl]benzene, 4,4'-dihydroxydiphenyl ether, 4,4'-dihydroxydiphenyl sulfone, 2,4'-dihydroxydiphenyl sulfone, 3,3'-dichloro-4,4'-dihydroxydiphenyl sulfone, 3,3'-diallyl-4,4'-dihydroxydiphenyl sulfone, 3,3'-dichloro-4,4'-dihydroxydiphenyl sulfide, methyl 2,2-bis(4-hydroxyphenyl)acetate, butyl 2,2-bis(4-hydroxyphenyl)acetate, 4,4'-thiobis(2-t-butyl-5-methylphenol), benzyl p-hydroxybenzoate, chlorobenzyl p-hydroxybenzoate, dimethyl 4-hydroxyphthalate, benzyl gallate, stearyl gallate, salicylanilide, 5-chlorosalicylanilide, etc. Among them, sulfonyl group-containing phenol derivatives are especially preferred because they are superior in color formability and image storage stability.

Examples of the aromatic carboxylic acids or derivatives thereof and metal salts thereof are zinc salicylate, 3,5-di-tert-butylsalicylic acid or zinc salt thereof, 4-octanoylaminosalicylic acid or zinc salt thereof, 4-decanoylaminosalicylic acid or zinc salt thereof, 3,5-di-α-phenethylsalicylic acid or zinc salt thereof, 4-[2-(4-methoxyphenoxy)ethoxy]salicylic acid or zinc salt thereof, 2-(p-toluenesulfonylamino)benzoic acid or zinc salt thereof, etc. Among them, salicylic acid or derivatives thereof and metal salts thereof represented by zinc salts are especially preferred because they are superior in color formability and image storage stability.

Examples of the N-sulfonylurea derivatives are N-(p-toluenesulfonyl)-N'-phenylurea, N-(p-toluene-sulfonyl)-N'-(p-tolyl)urea, 4,4'-bis(p-toluenesulfonylaminocarbonylamino)-diphenylmethane, etc.

As example of the process for producing the heat-sensitive recording material of the present invention, mention may be made of a process which comprises forming a heat-sensitive layer by coating the color forming dye precursor and the color developer as main components on a support.

The process for preparing a coating solution for containing the color forming dye precursor of the present invention and the color developer in the heat-sensitive recording layer includes, for example, a process which comprises dissolving or dispersing each of the compounds in a solvent or a dispersing medium and then mixing the resulting solutions or dispersions, a process which comprises mixing the compounds and then dissolving or dispersing the mixture in a solvent or a dispersing medium. If necessary, a dispersing agent may be used. When the dispersing medium is water, water-soluble polymers such as polyvinyl alcohol and various surface active agents may be used as the dispersing agent. In the case of aqueous dispersion, water-soluble organic solvents such as ethanol may be added. Furthermore, when the dispersing medium is an organic solvent such as hydrocarbons, lecithin, phosphate esters or the like may be used as the dispersing agent.

Moreover, for the purpose of improving strength of the heat-sensitive layer, a binder may be added to the heat-sensitive recording layer. As examples of the binder, mention may be made of water-soluble polymers such as starches, hydroxyethylcellulose, methylcellulose, carboxymethylcellulose, gelatin, casein, polyvinyl alcohol, modified polyvinyl alcohol, sodium polyacrylate, acrylic amide/acrylic ester copolymer, acrylic amide/acrylic ester/methacrylic acid terpolymer, alkali salts of styrene/maleic anhydride copolymer, and alkali salts of ethylene/maleic anhydride copolymer and latexes such as polyvinyl acetate, polyurethane, polyacrylic esters, styrene/butadiene copolymer, acrylonitrile/butadiene copolymer, methyl acrylate/butadiene copolymer, ethylene/vinyl acetate copolymer, ethylene/vinyl chloride copolymer, polyvinyl chloride, ethylene/vinylidene chloride copolymer and polyvinylidene chloride. These are not limiting.

Furthermore, a heat meltable substance can be contained in the heat-sensitive recording layer as a sensitizer for adjusting the sensitivity of the heat-sensitive recording layer. The sensitizers are preferably those having a melting point of 60–200° C., especially preferably those having a melting point of 80–180° C. Examples of them include waxes such as N-hydroxymethylstearamide, behenamide, stearamide and palmitamide, naphthol derivatives such as 2-benzyloxynaphthalene, biphenyl derivatives such as p-benzylbiphenyl and 4-allyloxybiphenyl, polyether compounds such as 1,2-bis(3-methylphenoxy)ethane, 2,2'-bis(4-methoxyphenoxy)diethyl ether and bis(4-methoxyphenyl) ether, and carbonic acid or oxalic acid diesters such as diphenyl carbonate, dibenzyl oxalate and bis(p-methylbenzyl) oxalate. These sensitizers may be used each alone or in combination of two or more. When these sensitizers are used in the heat-sensitive recording layer mainly composed of a color forming dye precursor of the present invention and a color developer in order to obtain a sufficient thermal responsiveness, they are used in an amount of preferably 20–400% by weight, more preferably 30–350% by weight based on the color forming dye precursor.

Furthermore, microencapsulation technique used for pressure-sensitive and heat-sensitive recording materials can also be applied to the present invention. For example, the dye precursor of the present invention is enclosed in microcapsules comprising polyurea film or polyurethane film synthesized by interfacial polymerization or recording elements other than the dye precursor of the present invention are similarly microencapsulated and these can be used for pressure-sensitive, heat-sensitive and light-sensitive recording materials.

Supports used for the heat-sensitive recording materials of the present invention include paper, various nonwoven fabrics, woven fabrics, synthetic resin films such as polyethylene terephthalate and polypropylene, papers laminated with synthetic resins such as polyethylene and polypropylene, synthetic papers, metallic foils, glasses and composite sheets comprising combination thereof. These can be optionally used depending on purposes. These are not limiting. These may be opaque, translucent or transparent. In order for the background showing white color or other specific colors, a white pigment, an organic dye or pigment or air bubbles may be contained in the support or on the surface part of the support. When aqueous coating is effected on films, etc. and hydrophilicity of the support is small and coating of the heat-sensitive recording layer is difficult, the surface may be rendered hydrophilic by corona discharge or the like or the surface may be coated with the same water-soluble polymer as used for binders, whereby the heat-sensitive recording layer can be easily adhered to the support.

The layer of the heat-sensitive recording layer of the present invention may comprise only the heat-sensitive recording layer. If necessary, a protective layer may be provided on the heat-sensitive recording layer or an intermediate layer containing at least one of water-soluble polymer, white or colored dye or pigment and hollow particle may be provided between the heat-sensitive recording layer and the support. In this case, the protective layer and/or the intermediate layer may comprise a plurality of layers, namely, two or more layers. The heat-sensitive recording layer may be multi-layer of two or more layers where each of the components is contained in one layer or the proportion of the components is changed in the respective layers. Furthermore, a material capable of electrically, optically or magnetically recording an information may be contained in the heat-sensitive recording layer and/or other layers and/or another side of the support on which the heat-sensitive recording layer is not present. In addition, a backcoat layer may be provided on the side of the support on which the heat-sensitive layer is not provided, for the prevention of blocking and curling and for antistatic purpose.

The method for forming the heat-sensitive recording material of the present invention is not limited and it can be formed by conventional methods. For example, there may be used coating apparatuses such as air-knife coater, blade coater, bar coater and curtain coater, and various printing machines of the types such as lithographic printing, letterpress printing, intaglio printing, flexographic printing, gravure printing, screen printing and hot-melting. Furthermore, the layers can be held by UV irradiation•EB irradiation in addition to usual drying step.

The heat-sensitive recording layer of the present invention can be obtained by a method of mixing the respective dispersions obtained by pulverizing the respective components and coating the mixture on a support, followed by drying, a method of mixing the respective solutions obtained by dissolving the respective components in solvents and coating the mixture on a support, followed by drying, and other methods. The drying conditions depend on the dispersing medium and solvent such as water. In addition, there is a method of mixing the respective components, heating the mixture to melt the meltable component and coating the mixture with heating.

Furthermore, the heat-sensitive recording layer and/or the protective layer and/or the intermediate layer may contain pigments such as diatomaceous earth, talc, kaolin, calcined kaolin, calcium carbonate, magnesium carbonate, titanium oxide, zinc oxide, silicon oxide, aluminum hydroxide, and urea-formaldehyde resin; waxes for preventing head from wearing and sticking, such as higher fatty acid metal salts, e.g., zinc stearate and calcium stearate, paraffin, oxidized paraffin, polyethylene, polyethylene oxide, stearic acid amide and castor wax; dispersing agents such as sodium dioctylsulfosuccinate; surface active agents; ultraviolet absorbers such as of benzophenone type and benzotriazole type; antioxidants such as of hindered phenol type; light stabilizers such as of hindered amine type; fluorescent dyes; and the like.

The present invention will be illustrated by the following non-limitative examples. The compound number is the number of the color forming dye precursors of the present invention which are enumerated in Tables 1, 2, 3 and 4.

EXAMPLE 1

Preparation of Compound 1-2

In a flask equipped with a stirrer, a condenser and a calcium chloride-drying tube were charged 10.4 g of 2-anilino-3-methyl-6-N,N-diethylaminofluoran (trademark: ODB manufactured by Yamamoto Kasei Co., Ltd.), 10.0 g of di-t-butyl dicarbonate, 4.6 g of triethylamine, 0.5 g of 4-dimethylaminopyridine and 120 ml of tetrahydrofuran, followed by stirring for 72 hours at room temperature to effect the reaction. The reaction mixture was concentrated under reduced pressure. Then, ethyl acetate was added thereto and the reaction mixture was washed twice with 20% aqueous sodium hydrogencarbonate solution. It was further washed with distilled water, and thereafter the organic layer was separated, dried over magnesium sulfate and then concentrated under reduced pressure. The concentrated product was recrystallized from diethyl ether/n-hexane to obtain 8.5 g of the desired compound (m.p. 143° C.). Infrared absorption spectrum of the compound is shown in FIG. 1.

EXAMPLE 2

Preparation of Compound 1-3

Figure 2:
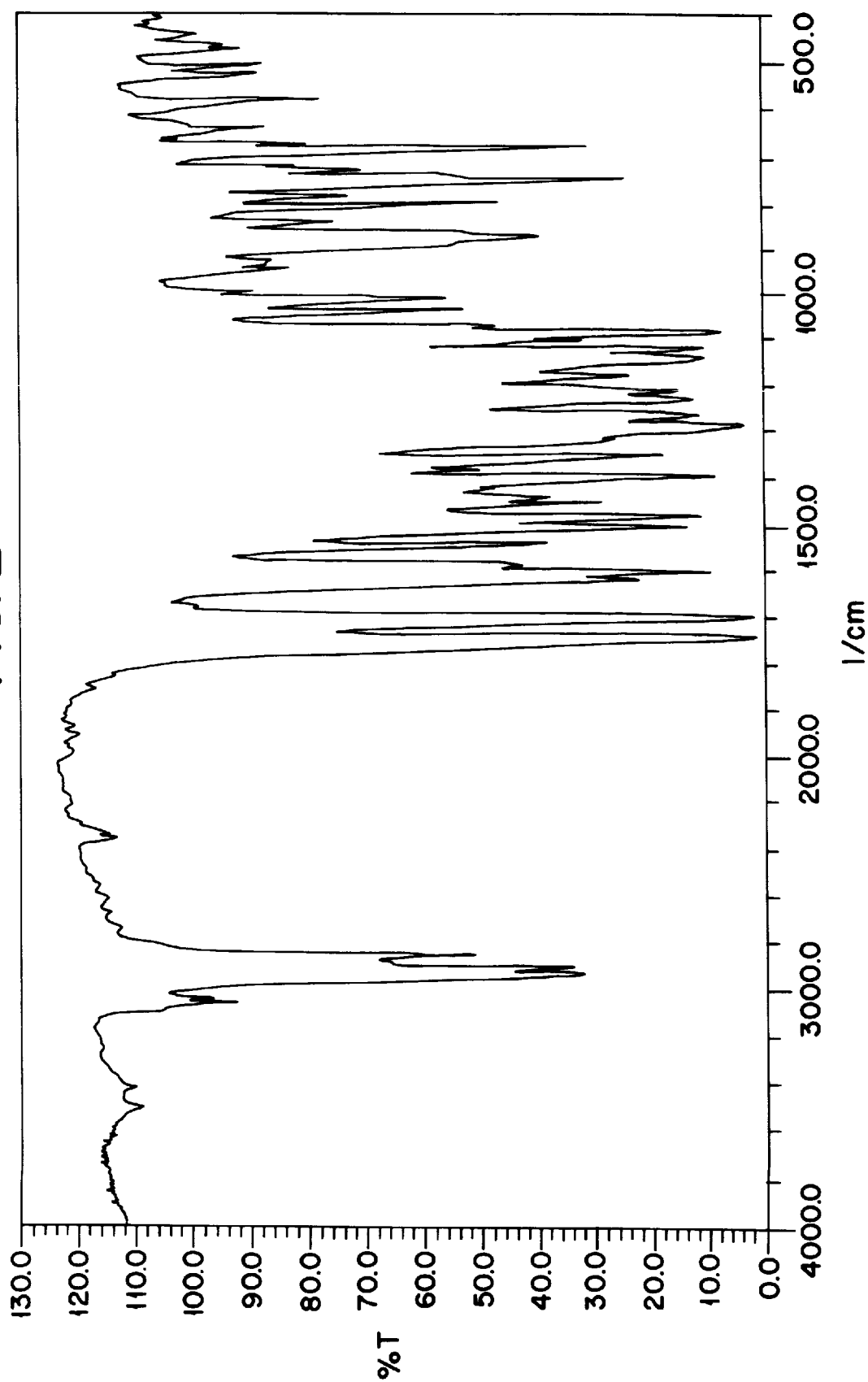
FIG. 2 is an infrared absorption spectrum of Compound 1-3 prepared in Example 2.

Preparation was carried out in the same manner as in Example 1, except that 11.6 g of 2-anilino-3-methyl-6-N, N-di-n-butylaminofluoran (trademark: ODB-2 manufactured by Yamamoto Kasei Co., Ltd.) was used in place of 2-anilino-3-methyl-6-N,N-diethylaminofluoran, whereby 8.3 g of the desired compound (m.p. 169° C.) was obtained. Infrared absorption spectrum of the compound is shown in FIG. 2.

EXAMPLE 3

Preparation of Compound 1-5

Figure 3:
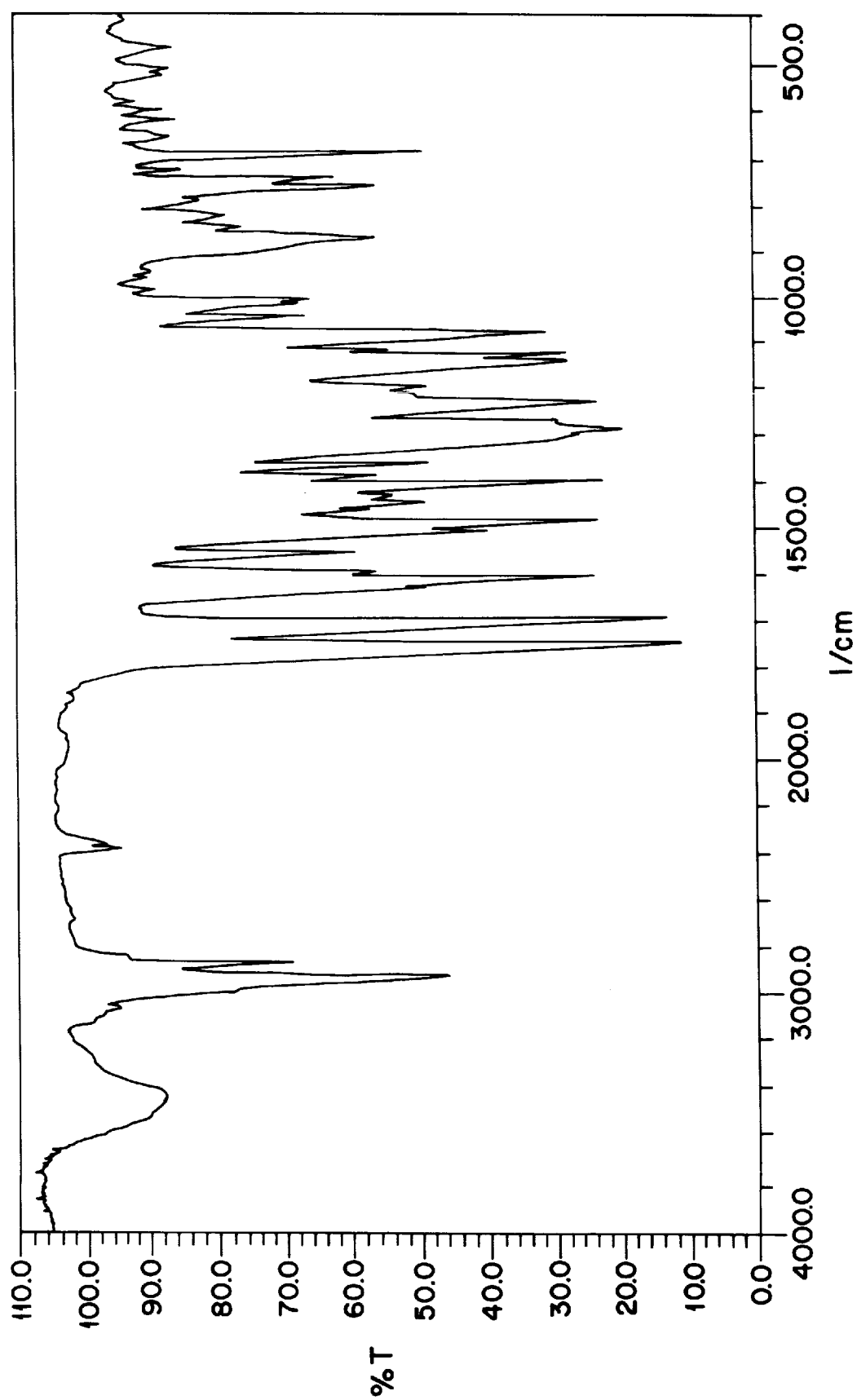
FIG. 3 is an infrared absorption spectrum of Compound 1-5 prepared in Example 3.

Preparation was carried out in the same manner as in Example 1, except that 11.3 g of 2-anilino-3-methyl-6-N-methyl-N-cyclohexylaminofluoran (trademark: PSD-150 manufactured by Nippon Soda Co., Ltd.) was used in place of 2-anilino-3-methyl-6-N,N-diethylaminofluoran, whereby 10.7 g of the desired compound (m.p. 170° C.) was obtained. Infrared absorption spectrum of the compound is shown in FIG. 3.

EXAMPLE 4

Preparation of Compound 1-6

Figure 4:
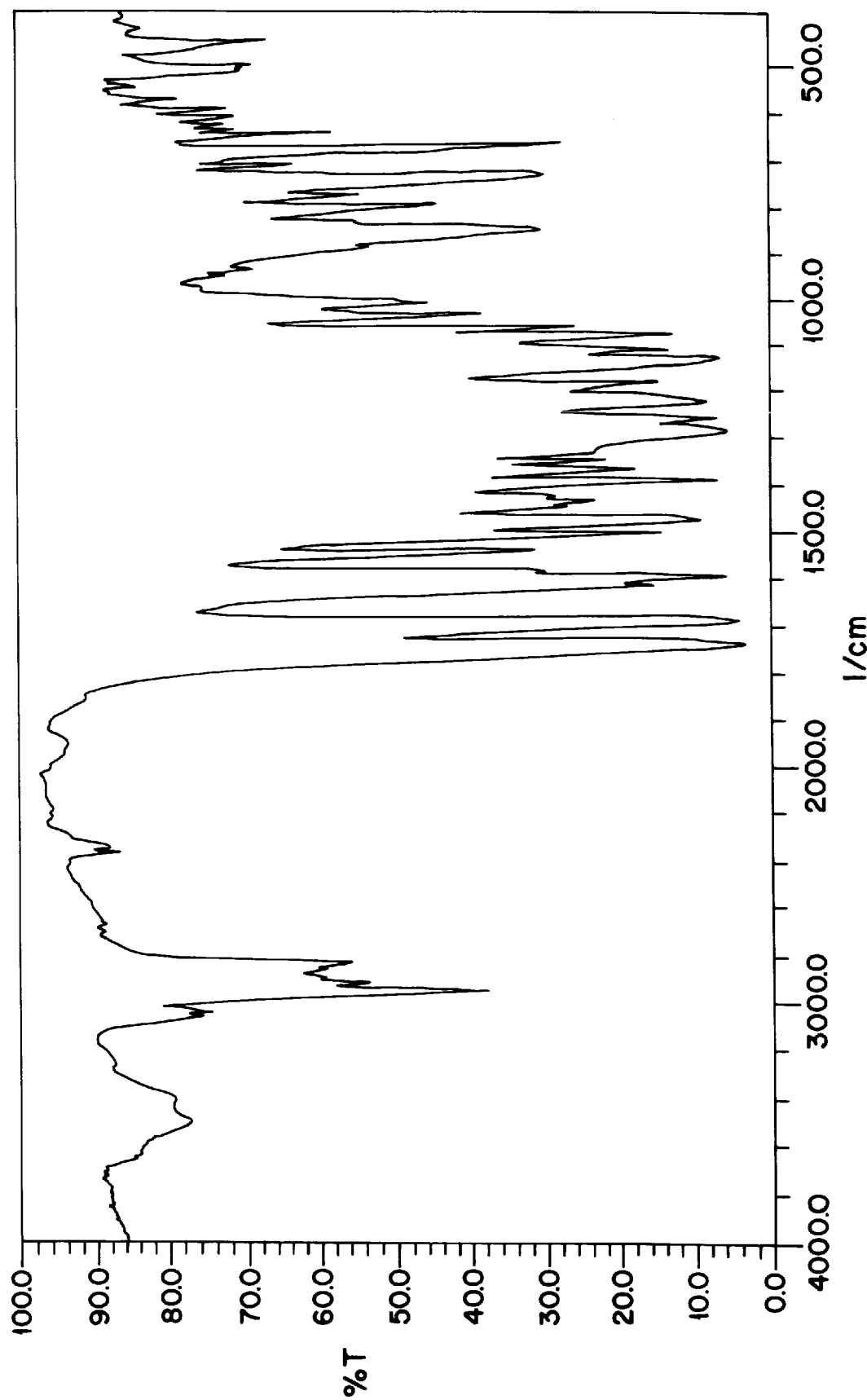
FIG. 4 is an infrared absorption spectrum of Compound 1-6 prepared in Example 4.

Preparation was carried out in the same manner as in Example 1, except that 10.3 g of 2-anilino-3-methyl-6-(1-pyrrolidinyl)fluoran (trademark: BK-14 manufactured by Yamada Kagaku Kogyo Co., Ltd.) was used in place of 2-anilino-3-methyl-6-N,N-diethylaminofluoran, whereby 11.4 g of the desired compound (m.p. 142° C.) was obtained. Infrared absorption spectrum of the compound is shown in FIG. 4.

EXAMPLE 5

Preparation of Compound 1-10

Figure 5:
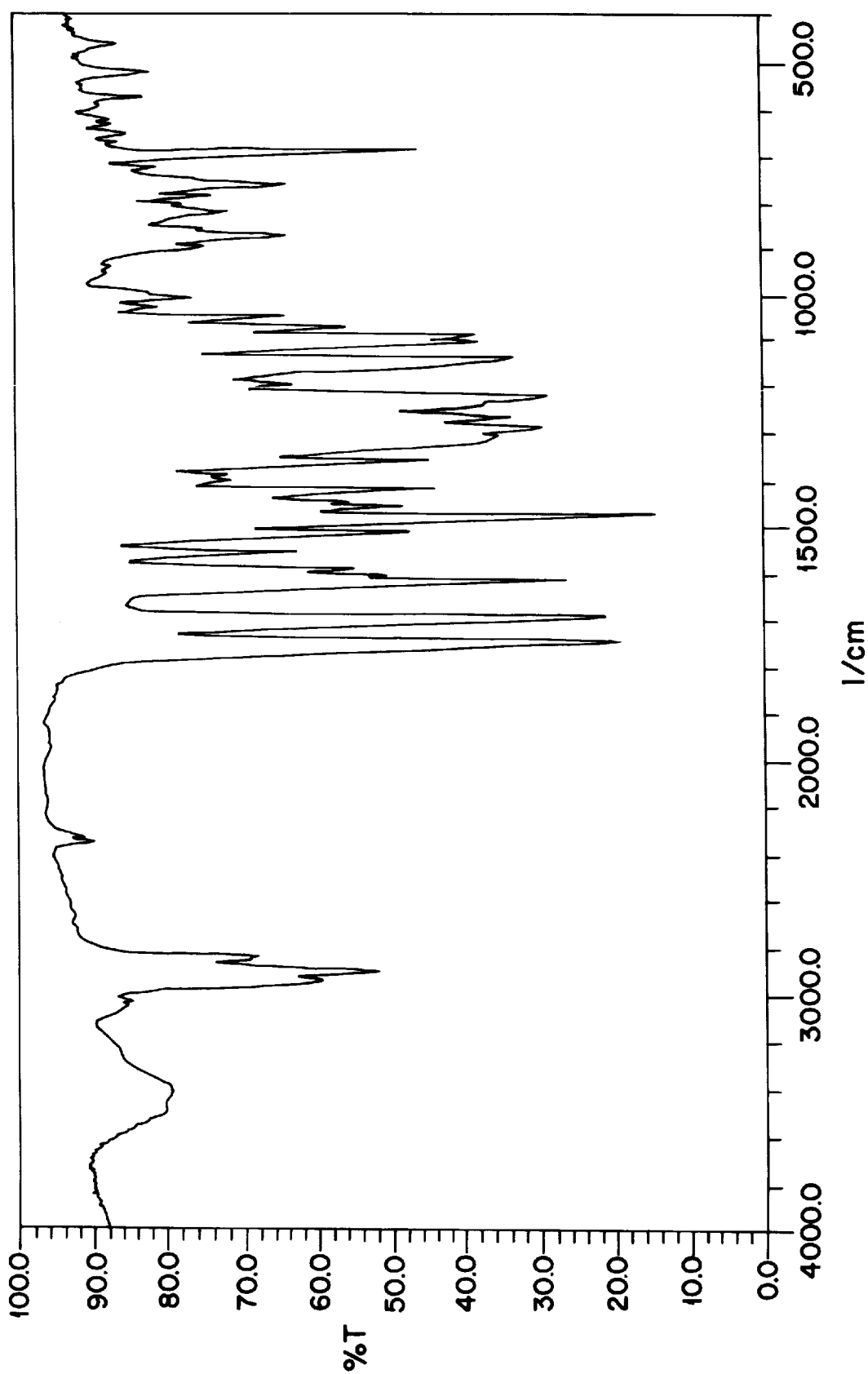
FIG. 5 is an infrared absorption spectrum of Compound 1-10 prepared in Example 5.

Preparation was carried out in the same manner as in Example 1, except that 11.3 g of 2-anilino-6-N-ethyl-N-n-hexylaminofluoran (trademark: Green-100 manufactured by Yamada Kagaku Kogyo Co., Ltd.) was used in place of 2-anilino-3-methyl-6-N,N-diethylaminofluoran, whereby 7.9 g of the desired compound (m.p. 67° C.) was obtained. Infrared absorption spectrum of the compound is shown in FIG. 5.

EXAMPLE 6

Preparation of Compound 1-11

Figure 6:
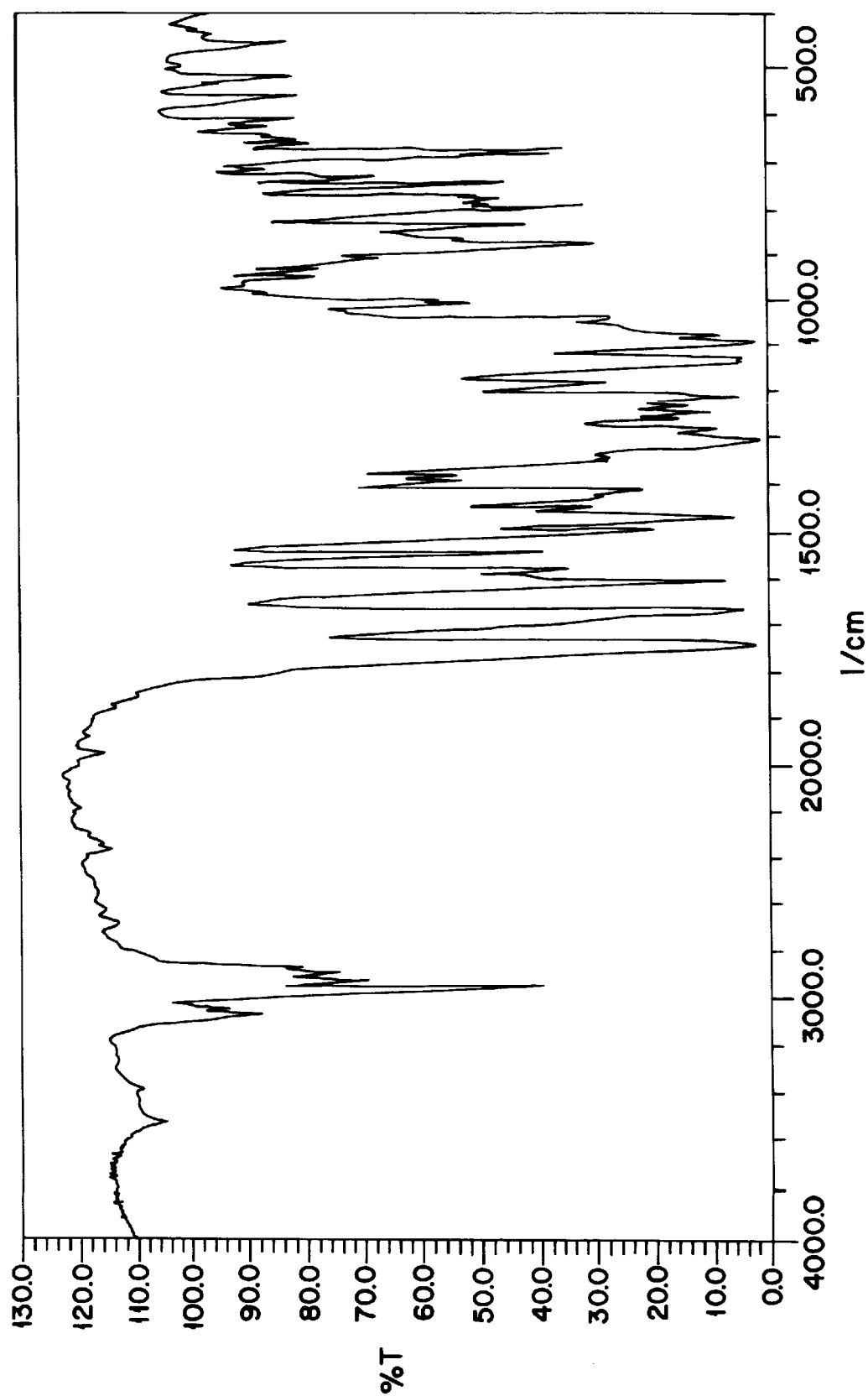
FIG. 6 is an infrared absorption spectrum of Compound 1-11 prepared in Example 6.

Preparation was carried out in the same manner as in Example 1, except that 11.6 g of 2-(3-trifluoromethylanilino)-6-N,N-diethylaminofluoran (trademark: Black-100 manufactured by Yamada Kagaku Kogyo Co., Ltd.) was used in place of 2-anilino-3-methyl-6-N,N-diethylaminofluoran, whereby 11.8 g of the desired compound (m.p. 165° C.) was obtained. Infrared absorption spectrum of the compound is shown in FIG. 6.

EXAMPLE 7

Preparation of Compound 1-12

Figure 7:
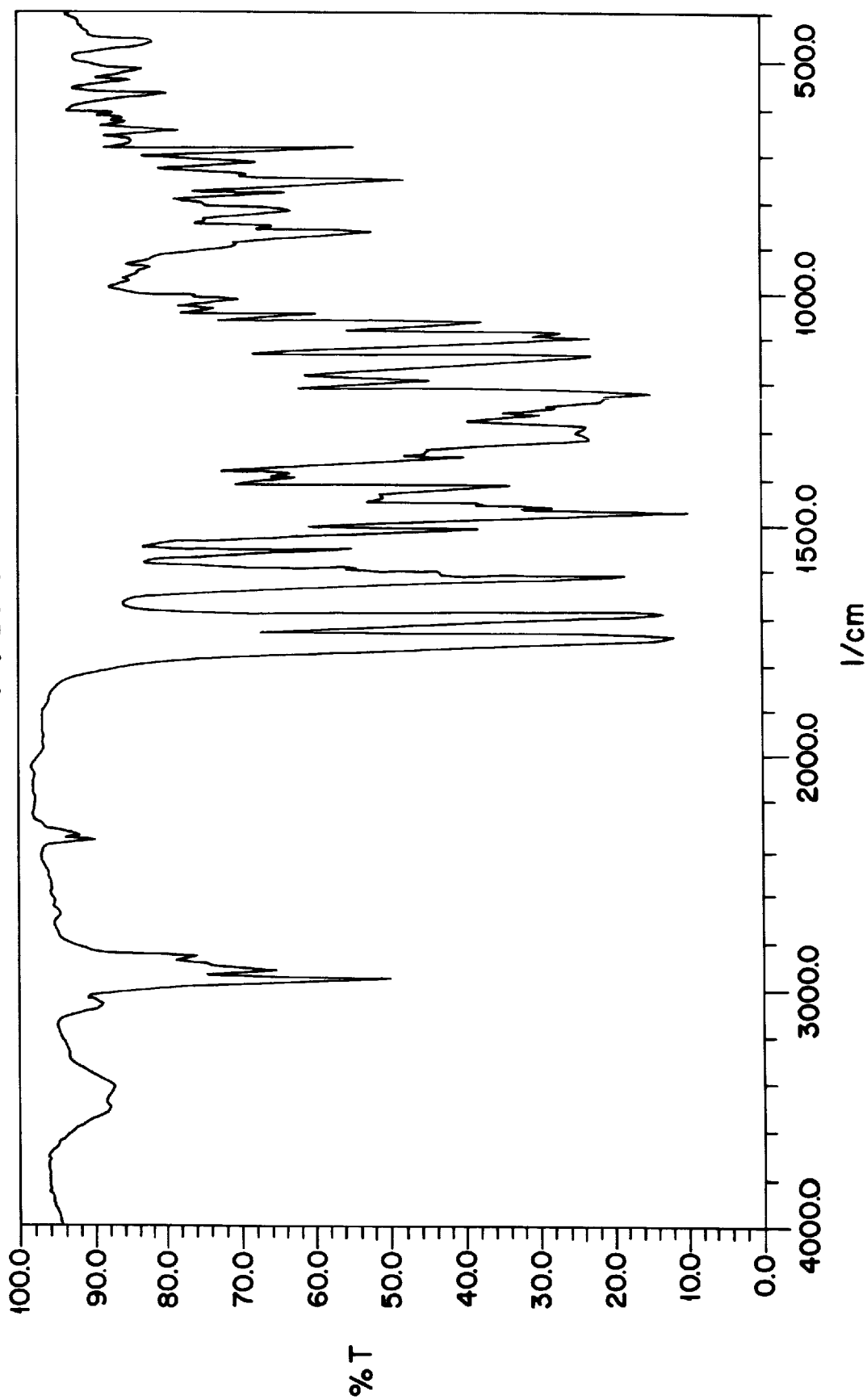
FIG. 7 is an infrared absorption spectrum of Compound 1-12 prepared in Example 7.

Preparation was carried out in the same manner as in Example 1, except that 10.8 g of 2-(2-chloroanilino)-6-N, N-diethylaminofluoran (trademark: Green-40 manufactured by Yamamoto Kasei Co., Ltd.) was used in place of 2-anilino-3-methyl-6-N,N-diethylaminofluoran, whereby 8.5 g of the desired compound (m.p. 101° C.) was obtained. Infrared absorption spectrum of the compound is shown in FIG. 7.

EXAMPLE 8

Preparation of Compound 2-2

Figure 8:
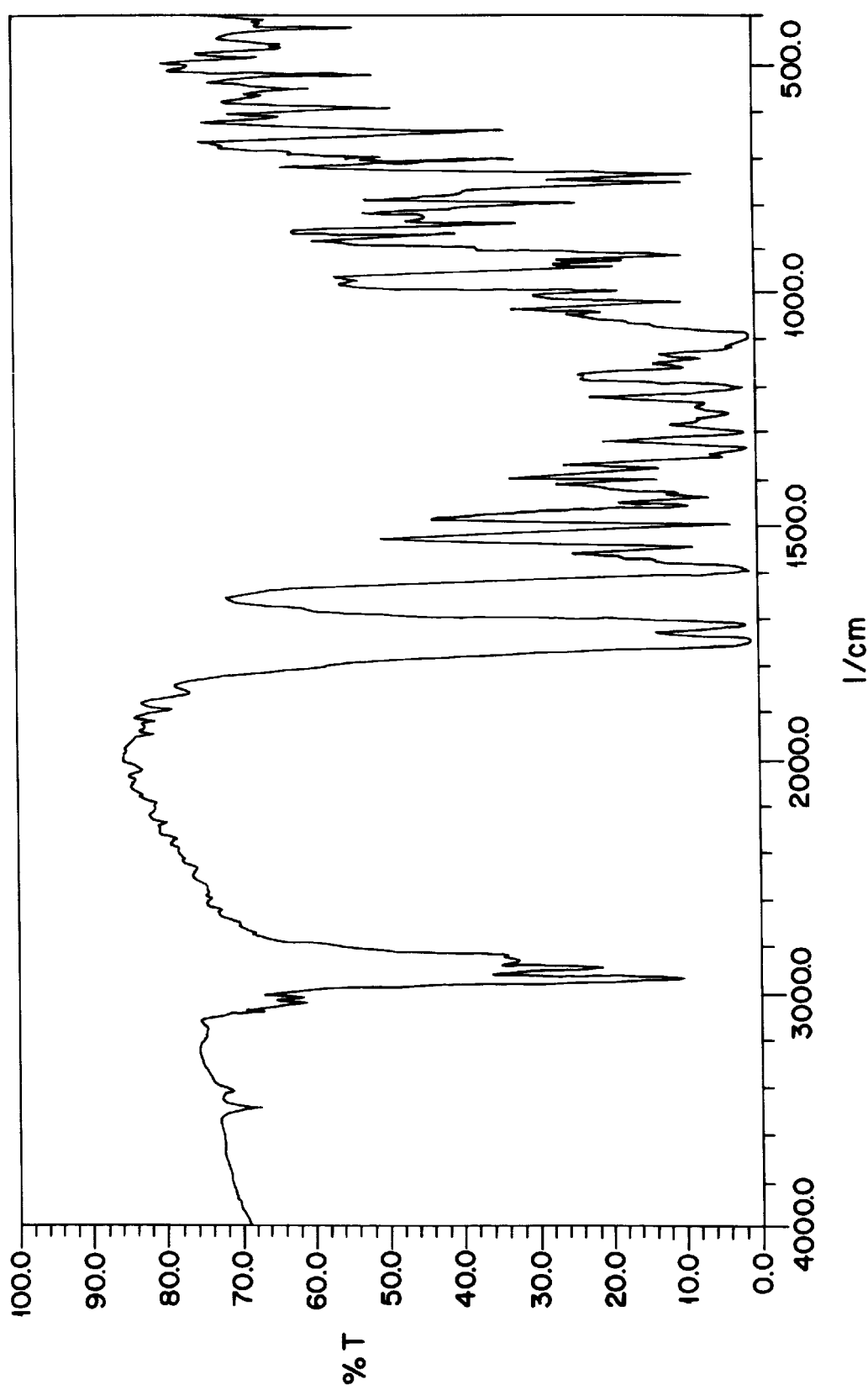
FIG. 8 is an infrared absorption spectrum of Compound 2-2 prepared in Example 8.

In a flask equipped with a stirrer, a condenser and a calcium chloride-drying tube were charged 11.8 g of 3-(4-diethylamino-2-ethoxyphenyl)-3-(2-methylindol-3-yl)-4-azaphthalide, 17.0 g of di-t-butyl dicarbonate, 7.9 g of triethylamine, 0.4 g of 4-dimethylaminopyridine and 150 ml of tetrahydrofuran, followed by stirring for 72 hours at room temperature to effect the reaction. The reaction mixture was concentrated under reduced pressure. Then, ethyl acetate was added thereto and the reaction mixture was washed twice with 20% aqueous sodium hydrogencarbonate solution. It was further washed with distilled water, and thereafter the organic layer was separated, dried over magnesium sulfate and then concentrated under reduced pressure. The concentrated product was recrystallized from diethyl ether/ n-hexane to obtain 9.2 g of the desired compound (m.p. 145° C.). Infrared absorption spectrum of the compound is shown in FIG. 8.

EXAMPLE 9

Preparation of Compound 2-3

Figure 9:
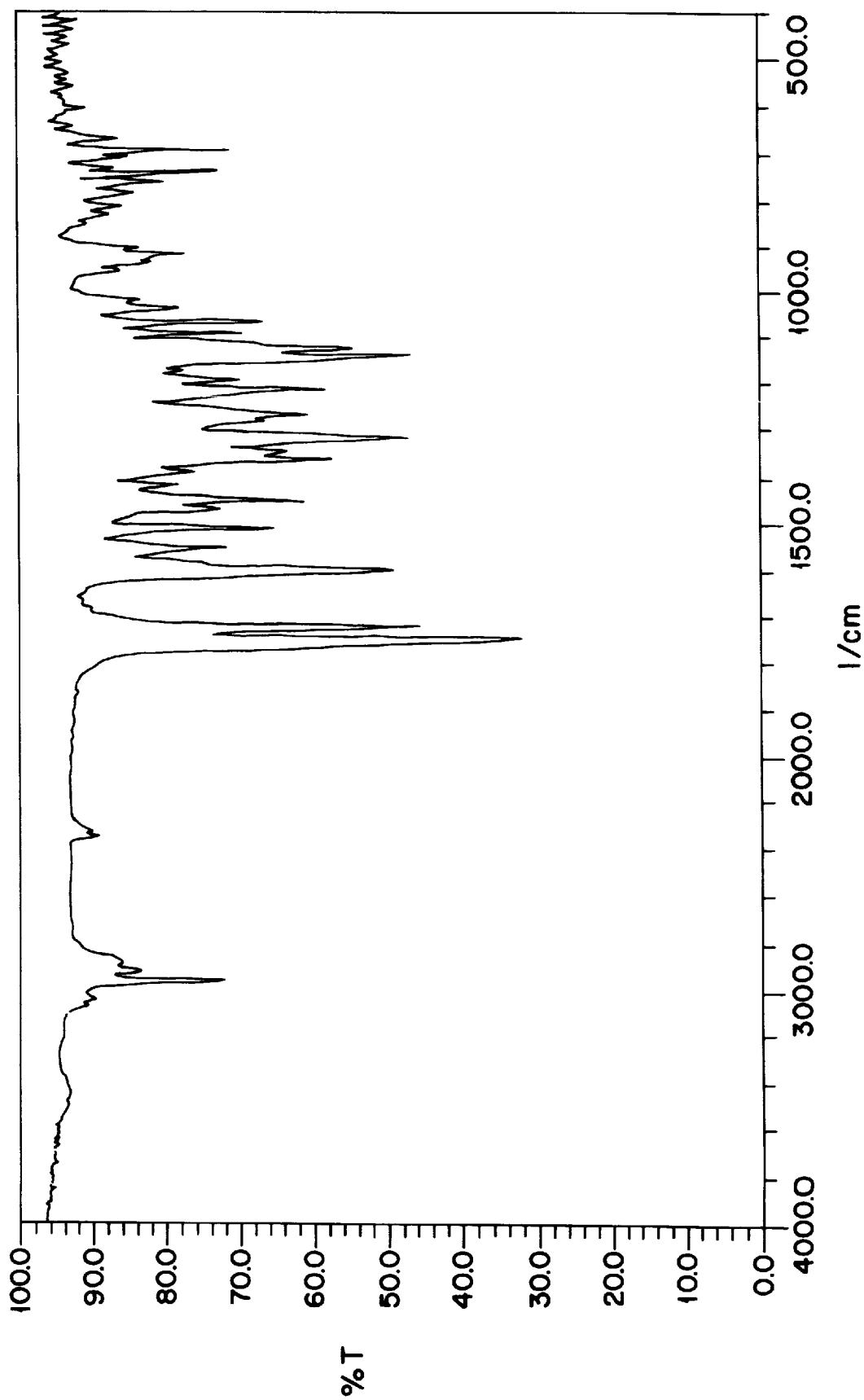
FIG. 9 is an infrared absorption spectrum of Compound 2-3 prepared in Example 9.

Preparation was carried out in the same manner as in Example 8, except that 13.5 g of 3-(4-diethylamino-2-ethoxyphenyl)-3-(2-phenylindol-3-yl)-4-azaphthalide was used in place of 3-(4-diethylamino-2-ethoxyphenyl)-3-(2-methylindol-3-yl)-4-azaphthalide, whereby 8.7 g of the desired compound (m.p. 147° C.) was obtained. Infrared absorption spectrum of the compound is shown in FIG. 9.

EXAMPLE 10

Preparation of Compound 3-2

Figure 10:
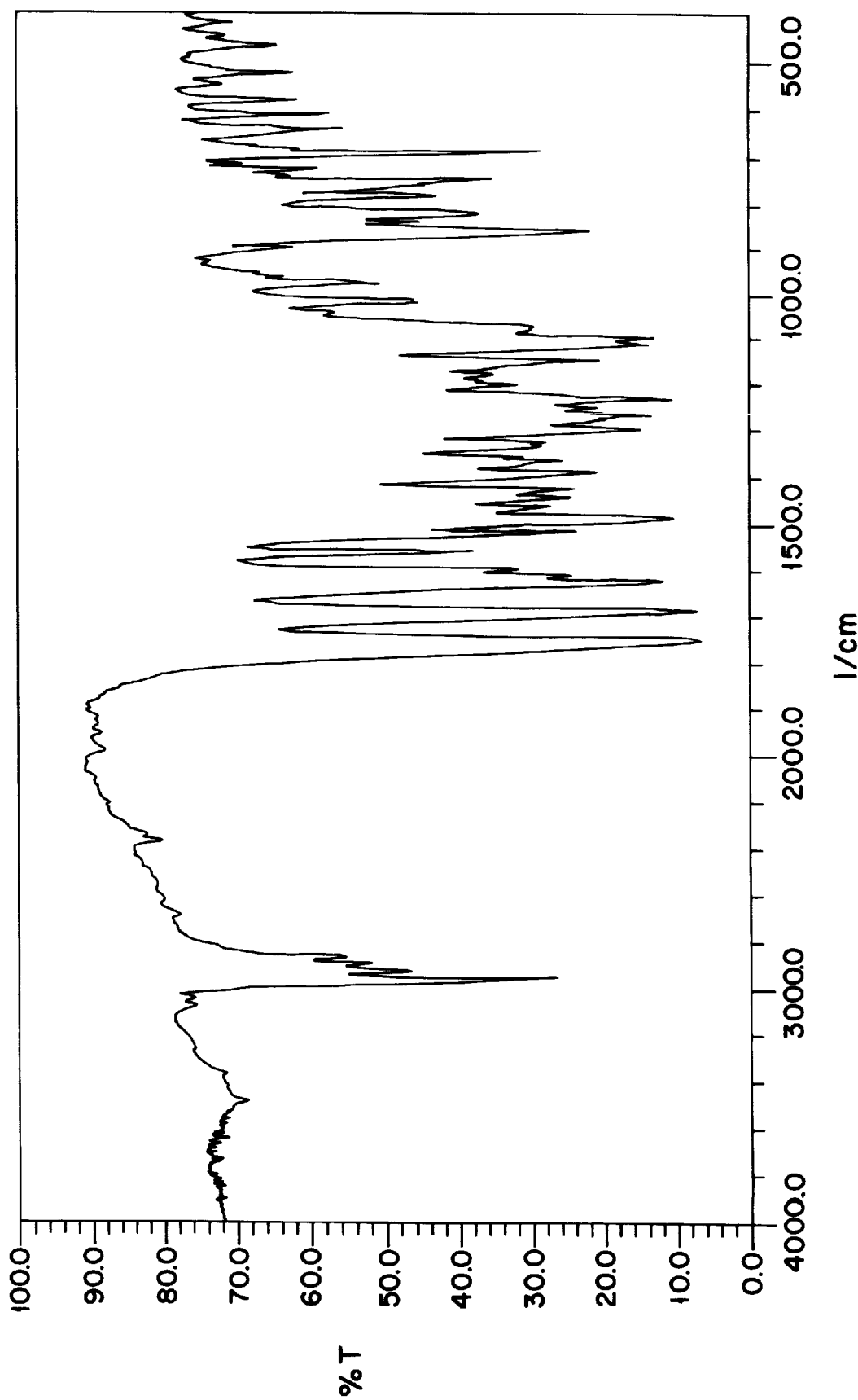
FIG. 10 is an infrared absorption spectrum of Compound 3-2 prepared in Example 10.

In a flask equipped with a stirrer, a condenser and a calcium chloride-drying tube were charged 10.0 g of 2-ethylamino-6-N,N-diethylaminofluoran, 15.8 g of di-t-butyl dicarbonate, 7.2 g of triethylamine, 0.6 g of 4-dimethylaminopyridine and 120 ml of tetrahydrofuran, followed by stirring for 24 hours at room temperature to effect the reaction. The reaction mixture was concentrated under reduced pressure. Then, ethyl acetate was added thereto and the reaction mixture was washed twice with 20% aqueous sodium hydrogencarbonate solution. It was further washed with distilled water, and thereafter the organic layer was separated, dried over magnesium sulfate and then concentrated under reduced pressure. The concentrated product was recrystallized from diethyl ether/n-hexane to obtain 7.5 g of the desired compound (m.p. 123° C.). Infrared absorption spectrum of the compound is shown in FIG. 10.

EXAMPLE 11

Preparation of Compound 4-2

Figure 11:
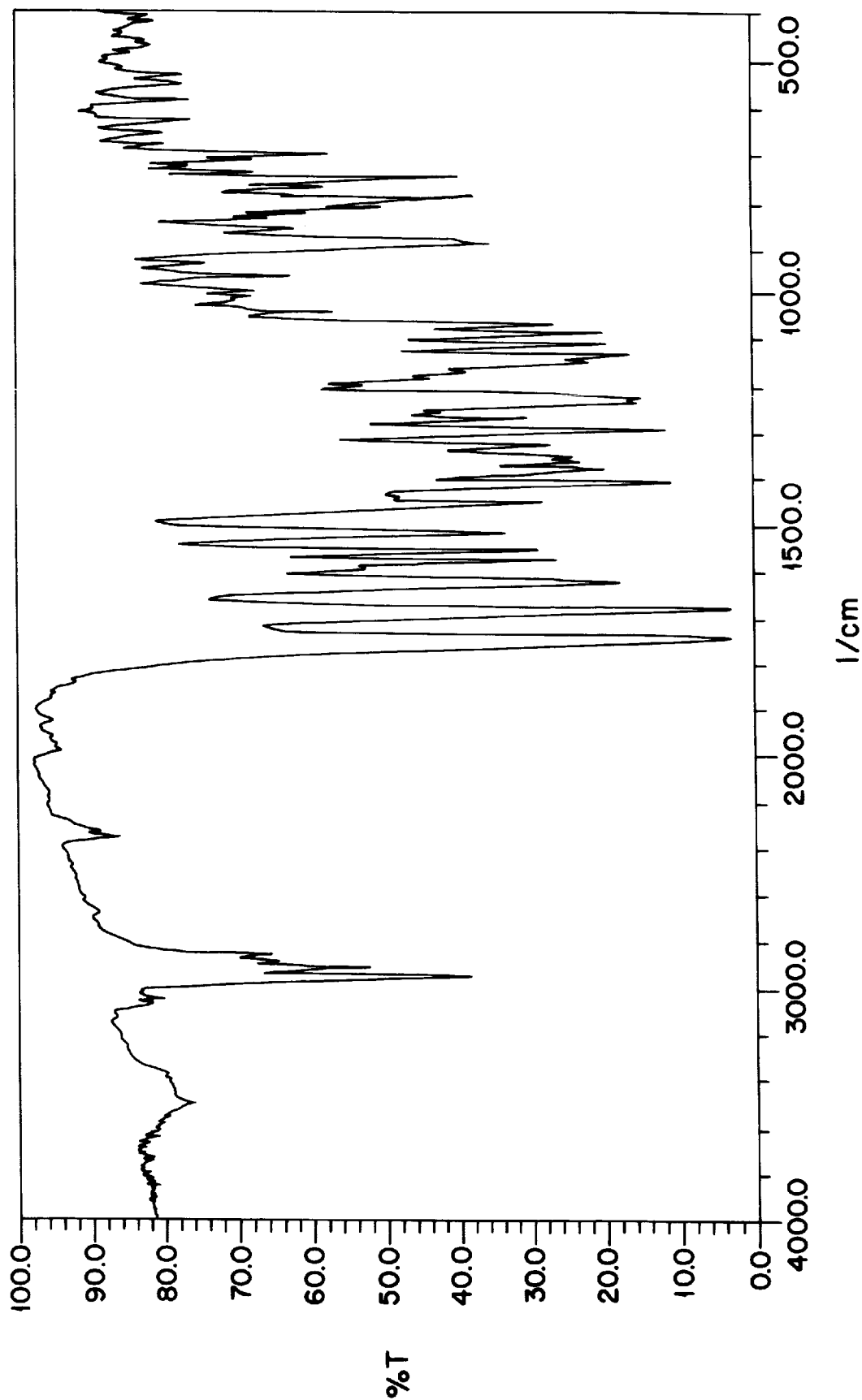
FIG. 11 is an infrared absorption spectrum of Compound 4-2 prepared in Example 11.

In a flask equipped with a stirrer, a condenser and a calcium chloride-drying tube were charged 10.0 g of 4-ethylamino-8-N,N-diethylaminobenzo[a]fluoran, 15.2 g of di-t-butyl dicarbonate, 6.6 g of triethylamine, 0.5 g of 4-dimethylaminopyridine and 120 ml of tetrahydrofuran, followed by stirring for 24 hours at room temperature to effect the reaction. The reaction mixture was concentrated under reduced pressure. Then, ethyl acetate was added thereto and the reaction mixture was washed twice with 20% aqueous sodium hydrogencarbonate solution. It was further washed with distilled water, and thereafter the organic layer was separated, dried over magnesium sulfate and then concentrated under reduced pressure. The concentrated product was recrystallized from diethyl ether/n-hexane to obtain 7.2 g of the desired compound (m.p. 204° C. (decomposition)). Infrared absorption spectrum of the compound is shown in FIG. 11.

(1) Evaluation of the color forming dye precursors represented by the formula (1)

EXAMPLE 12

Production of heat-sensitive recording material: (All parts in the following description are by weight):

(a) Preparation of heat-sensitive coating solution (Liquid A): 60 parts of 2-(N-t-butoxycarbonylanilino)-3-methyl-6-N,N-diethylaminofluoran (Compound 1-2) prepared in Example 1 was pulverized by a paint conditioner together with 140 parts of 2.2% aqueous polyvinyl alcohol solution to obtain a dye precursor dispersion.

(Liquid B): Then, 60 parts of 2,2-bis(4-hydroxyphenyl) propane was pulverized by a paint conditioner together with 140 parts of 2.2% aqueous polyvinyl alcohol solution to obtain a color developer dispersion.

(Liquid C): Furthermore, 60 parts of 2-benzyloxynaphthalene was pulverized by a paint conditioner together with 140 parts of 2.2% aqueous polyvinyl alcohol solution to obtain a sensitizer dispersion.

(Liquid D): Moreover, 30 parts of calcium carbonate and 70 parts of 0.4% aqueous polyvinyl alcohol solution were pulverized in the same manner as above.

The four dispersions of A (10.5 parts), B (20.9 parts), C (20.9 parts) and D (29.9 parts) were mixed, and to the mixture were added 2.2 parts of 40% zinc stearate dispersion (manufactured by Chukyo Yushi Co., Ltd.), 51.1 parts of 10% aqueous polyvinyl alcohol solution and 14.6 parts of water, followed by well mixing them to obtain a heat-sensitive coating solution.

(b) Preparation of support to be coated with the heat-sensitive coating solution A coating solution composed of 100 parts of calcined kaolin, 24 parts of a 50% aqueous dispersion of styrene-butadiene latex and 200 parts of water was coated on a base paper of 40 g/m² in basis weight at a solid coating amount of 9 g/m² and the coat was dried to obtain a support.

(c) Production of heat-sensitive recording material

The coating solution prepared in (a) was coated on the support prepared in (b) at a solid coating amount of 5.0 g/m² and treated by a supercalender to obtain a heat-sensitive recording material.

EXAMPLE 13

A heat-sensitive recording material was obtained in the same manner as in Example 12, except that 2-(N-t-butoxycarbonylanilino)-3-methyl-6-N,N-di-n-butylaminofluoran (Compound 1-3) prepared in Example 2 was used in place of 2-(N-t-butoxycarbonylanilino)-3-methyl-6-N,N-diethylaminofluoran (Compound 1-2) used in Example 12 and 4-hydroxy-4'-isopropoxydiphenyl sulfone was used in place of 2,2-bis(4-hydroxyphenyl)propane.

EXAMPLE 14

A heat-sensitive recording material was obtained in the same manner as in Example 13, except that 2-(3-trifluoromethyl-N-t-butoxycarbonyl)anilino-6-N,N-diethylaminofluoran (Compound 1-11) prepared in Example 6 was used in place of 2-(N-t-butoxycarbonylanilino)-3-methyl-6-N,N-di-n-butylaminofluoran (Compound 1-3) used in Example 13.

EXAMPLE 15

A heat-sensitive recording material was obtained in the same manner as in Example 13, except that zinc 4-n-octanoylaminosalicylate was used in place of 4-hydroxy-4'-isopropoxydiphenyl sulfone used in Example 13.

COMPARATIVE EXAMPLE 1

A heat-sensitive recording material was obtained in the same manner as in Example 12, except that 2-(N-acetylanilino)-3-methyl-6-N,N-di-n-butylaminofluoran was used in place of 2-(N-t-butoxycarbonylanilino)-3-methyl-6-N,N-diethylaminofluoran (Compound 1-2) used in Example 12.

EXAMPLE 16

Test on Color Forming Characteristics

The heat-sensitive recording materials obtained in Examples 12–15 and Comparative Example 1 were subjected to printing with an applied energy in the range of 14–154 mj/mm² using a heat-sensitive facsimile printing tester TH-PMD (manufactured by Okura Denki Co., Ltd.) having a printing head LH4409 (manufactured by TDK Electronics Co., Ltd.). Density of the resulting color images was measured by a densitometer Macbeth RD918.

The results of the test on the heat-sensitive recording materials of Examples 12–15 and Comparative Example 1 are shown in Table 5. The low-temperature formed color image and the high-temperature formed color image were formed under the conditions of applied energy of 38.5 mj and 140 mj, respectively. The density of printed portions was measured using an amber filter for black image and a green filter for red image.

TABLE 5

|  | Low-temperature formed color image | | High-temperature formed color image | |
|---|---|---|---|---|
|  | Color | Density | Color | Density |
| Example 12 | Red | 1.26 | Black | 0.98 |
| Example 13 | Red | 1.28 | Black | 1.10 |
| Example 14 | Red | 1.18 | Black | 1.03 |
| Example 15 | Red | 1.27 | Black | 1.28 |
| Comparative Example 1 | Red | 1.22 | Red | 1.25 |

(2) Evaluation of color forming dye precursors represented by the formula (2)

EXAMPLE 17

A heat-sensitive recording material was obtained in the same manner as in Example 12, except that 3-(4-diethylamino-2-ethoxyphenyl)-3-(1-t-butoxycarbonyl-2-methylindol-3-yl)-4-azaphthalide (Compound 2-2) prepared in Example 8 was used in place of 2-(N-t-butoxycarbonylanilino)-3-methyl-6-N,N-diethylaminofluoran (Compound 1-2) used in Example 12.

EXAMPLE 18

A heat-sensitive recording material was obtained in the same manner as in Example 17, except that 3-(4-diethylamino-2-ethoxyphenyl)-3-(1-t-butoxycarbonyl-2-phenylindol-3-yl)-4-azaphthalide (Compound 2-3) prepared in Example 9 was used in place of 3-(4-diethylamino-2-ethoxyphenyl)-3-(1-t-butoxycarbonyl-2-methylindol-3-yl)-4-azaphthalide (Compound 2-2) used in Example 17 and 4-hydroxy-4'-isopropoxydiphenyl sulfone was used in place of 2,2-bis(4-hydroxyphenyl)propane.

EXAMPLE 19

A heat-sensitive recording material was obtained in the same manner as in Example 18, except that zinc 4-n-octanoylaminosalicylate was used in place of 4-hydroxy-4'-isopropoxydiphenyl sulfone used in Example 18.

COMPARATIVE EXAMPLE 2

A heat-sensitive recording material was obtained in the same manner as in Example 17, except that 3-(4-diethylamino-2-ethoxyphenyl)-3-(1-ethyl-2-methylindol-3-yl)-4-azaphthalide (trademark: Blue-63 manufactured by Yamamoto Kasei Co., Ltd.) was used in place of 3-(4-diethylamino-2-ethoxyphenyl)-3-(1-t-butoxycarbonyl-2-methylindol-3-yl)-4-azaphthalide (Compound 2-2) used in Example 17.

EXAMPLE 20

Test on Color Forming Characteristics

The heat-sensitive recording materials obtained in Examples 17–19 and Comparative Example 2 were subjected to printing under the same conditions as in Example 16, and density of the resulting color images was measured using a densitometer Macbeth RD918.

The results of the test on color forming characteristics of the heat-sensitive recording materials obtained in Examples 17–19 and Comparative Example 2 are shown in Table 6. The low-temperature formed color image and the high-temperature formed color image were formed under the conditions of applied energy of 38.5 mj and 140 mj, respectively. The density of the printed portions was measured using a yellow filter for blue image and a green filter for red image.

TABLE 6

|  | Low-temperature formed color image | | High-temperature formed color image | |
|---|---|---|---|---|
|  | Color | Density | Color | Density |
| Example 17 | Reddish purple | 1.11 | Blue | 0.88 |
| Example 18 | Reddish purple | 1.15 | Blue | 0.96 |
| Example 19 | Reddish purple | 1.26 | Blue | 1.13 |
| Comparative Example 2 | Blue | 1.24 | Blue | 1.25 |

(3) Evaluation of color forming dye precursors represented by the formula (3)

EXAMPLE 21

A heat-sensitive recording material was obtained in the same manner as in Example 12, except that 2-(N-t-butoxycarbonyl)ethylamino-6-N,N-diethylaminofluoran (Compound 3-2) prepared in Example 10 was used in place of 2-(N-t-butoxycarbonylanilino)-3-methyl-6-N,N-diethylaminofluoran (Compound 1-2) used in Example 12.

EXAMPLE 22

A heat-sensitive recording material was obtained in the same manner as in Example 21, except that zinc 4-n-octanoylaminosalicylate was used in place of 2,2-bis(4-hydroxyphenyl)propane used in Example 21.

COMPARATIVE EXAMPLE 3

A heat-sensitive recording material was obtained in the same manner as in Example 21, except that 2-(N-acetyl)ethylamino-6-N,N-diethylaminofluoran was used in place of 2-(N-t-butoxycarbonyl)ethylamino-6-N,N-diethylaminofluoran (Compound 3-2) used in Example 21.

EXAMPLE 23

Test on Color Forming Characteristics

The heat-sensitive recording materials obtained in Examples 21 and 22 and Comparative Example 3 were subjected to printing under the same conditions as in Example 16, and density of the resulting color images was measured using a densitometer Macbeth RD918.

The results of the test on color forming characteristics of the heat-sensitive recording materials obtained in Examples 21 and 22 and Comparative Example 3 are shown in Table 7. The low-temperature formed color image and the high-temperature formed color image were formed under the conditions of applied energy of 38.5 mj and 140 mj, respectively. The density of the printed portions was measured using an amber filter for black image and a green filter for red image.

TABLE 7

|  | Low-temperature formed color image | | High-temperature formed color image | |
| --- | --- | --- | --- | --- |
|  | Color | Density | Color | Density |
| Example 21 | Red | 1.21 | Black | 0.98 |
| Example 22 | Red | 1.23 | Black | 1.25 |
| Comparative Example 3 | Red | 1.23 | Red | 1.24 |

(4) Evaluation of color forming dye precursors represented by the formula (4)

EXAMPLE 24

A heat-sensitive recording material was obtained in the same manner as in Example 12, except that 4-(N-t-butoxycarbonyl)ethylamino-8-N,N-diethylamino-benzo[a]fluoran (Compound 4-2) prepared in Example 11 was used in place of 2-(N-t-butoxycarbonylanilino)-3-methyl-6-N,N-diethylaminofluoran (Compound 1-2) used in Example 12.

EXAMPLE 25

A heat-sensitive recording material was obtained in the same manner as in Example 24, except that zinc 4-n-octanoylaminosalicylate was used in place of 2,2-bis(4-hydroxyphenyl)propane used in Example 24.

COMPARATIVE EXAMPLE 4

A heat-sensitive recording material was obtained in the same manner as in Example 24, except that 4-(N-acetyl)ethylamino-8-N,N-diethylaminobenzo[a]fluoran was used in place of 4-(N-t-butoxycarbonyl)ethylamino-8-N,N-diethylamino-benzo[a]fluoran (Compound 4-2) used in Example 24.

EXAMPLE 26

Test on Color Forming Characteristics

The heat-sensitive recording materials obtained in Examples 24 and 25 and Comparative Example 4 were subjected to printing under the same conditions as in Example 16, and density of the resulting color images was measured using a densitometer Macbeth RD918.

The results of the test on color forming characteristics of the heat-sensitive recording materials obtained in Examples 24 and 25 and Comparative Example 4 are shown in Table 8. The low-temperature formed color image and the high-temperature formed color image were formed under the conditions of applied energy of 38.5 mj and 140 mj, respectively. The density of the printed portions was measured using an a yellow filter for blue image and a green filter for red image.

TABLE 8

|  | Low-temperature formed color image | | High-temperature formed color image | |
| --- | --- | --- | --- | --- |
|  | Color | Density | Color | Density |
| Example 24 | Reddish purple | 1.05 | Blue | 0.83 |
| Example 25 | Reddish purple | 1.10 | Blue | 0.87 |
| Comparative Example 4 | Reddish purple | 1.22 | Reddish purple | 1.22 |

The fluoran compounds and indolylphthalide compounds represented by the formulas (1), (2), (3) and (4) each singly develop two colors upon color forming reaction with one kind of an electron accepting color developer depending on change in the heat energy applied. Furthermore, the resulting respective color images are distinct. Therefore, these compounds are useful as color formers used in color forming recording materials such as heat-sensitive recording materials. Furthermore, by using these fluoran compounds and indolylphthalide compounds, even when the heat-sensitive recording layer comprises a single layer, images of at least two colors differing in hue can be obtained due to difference in heat energy applied.

What is claimed is:

1. A color forming dye precursor represented by the following formula (1), (2), (3) or (4) which undergoes change in chemical structure by heat energy:

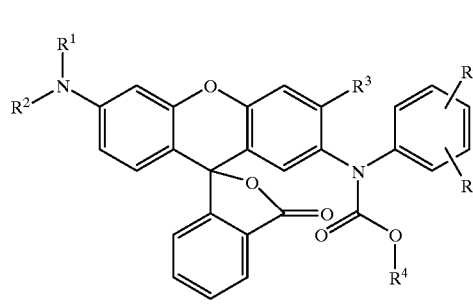

(1)

wherein each of $R^1$ and $R^2$ independently represents an alkyl group, a cycloalkyl group, an alkoxyalkyl group, a tetrahydrofurfuryl group or a substituted or unsubstituted phenyl group, $R^1$ and $R^2$ may link to each other to form a heterocyclic ring together with the nitrogen atom which bonds to $R^1$ and $R^2$; $R^3$ represents a hydrogen atom or a lower alkyl group; $R^4$ represents a tertiary hydrocarbon group or —$(CH_2)_2$—Y in which Y represents an electron attracting group having a positive σ in Hammett's rule; and each of $R^5$ and $R^6$ independently represents a hydrogen atom, a lower alkyl group, a halogen atom, a trifluoromethyl group or an acetyl group, (2)

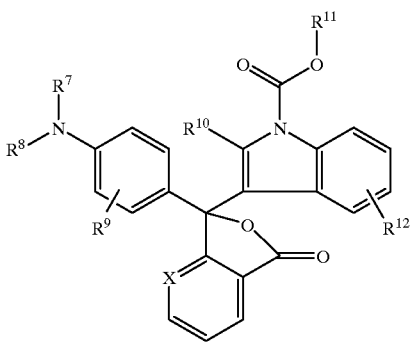

wherein each of $R^7$ and $R^8$ independently represents an alkyl group, a cycloalkyl group, an alkoxyalkyl group, a tetrahydrofurfuryl group or a substituted or unsubstituted phenyl group, $R^7$ and $R^8$ may link to each other to form a heterocyclic ring together with the nitrogen atom which bonds to $R^7$ and $R^8$; $R^9$ represents a hydrogen atom, a lower alkyl group or a lower alkoxy group; $R^{10}$ represents a hydrogen atom, a lower alkyl group or a substituted or unsubstituted phenyl group; $R^{11}$ represents a tertiary hydrocarbon group or —$(CH_2)_2$—Y in which Y represents an electron attracting group having a positive σ in Hammett's rule; $R^{12}$ represents a hydrogen atom, a lower alkyl group, a halogen atom, a trifluoromethyl group or an acetyl group; and X represents a nitrogen atom or a methine group, (3)

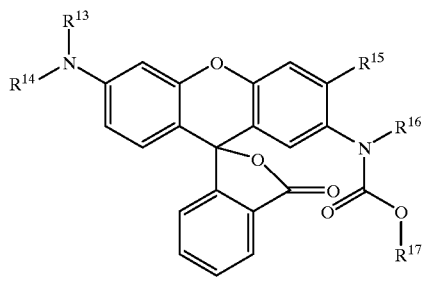

wherein each of $R^{13}$ and $R^{14}$ independently represents an alkyl group, a cycloalkyl group, an alkoxyalkyl group, a tetrahydrofurfuryl group or a substituted or unsubstituted phenyl group, $R^{13}$ and $R^{14}$ may link to each other to form a heterocyclic ring together with the nitrogen atom which bonds to $R^{13}$ and $R^{14}$; $R^{15}$ represents a hydrogen atom, a lower alkyl group or a lower alkoxy group; $R^{16}$ represents a hydrocarbon group of 1–18 carbon atoms; and $R^{17}$ represents a tertiary hydrocarbon group or —$(CH_2)_2$—Y in which Y represents an electron attracting group having a positive σ in Hammett's rule, (4)

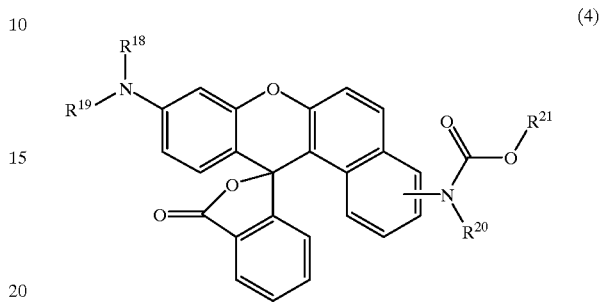

wherein each of $R^{18}$ and $R^{19}$ independently represents an alkyl group, a cycloalkyl group, an alkoxyalkyl group, a tetrahydrofurfuryl group or a substituted or unsubstituted phenyl group, $R^{18}$ and $R^{19}$ may link to each other to form a heterocyclic ring together with the nitrogen atom which bonds to $R^{18}$ and $R^{19}$; $R^{20}$ represents a hydrocarbon group of 1–18 carbon atoms; $R^{21}$ represents a tertiary hydrocarbon group or —$(CH_2)_2$—Y in which Y represents an electron attracting group having a positive σ in Hammett's rule; and the position of the substituent —$N(R^{20})$—$COOR^{21}$ is 2- or 4-position.

2. A color forming dye precursor according to claim 1, wherein $R^4$ is selected from the group consisting of

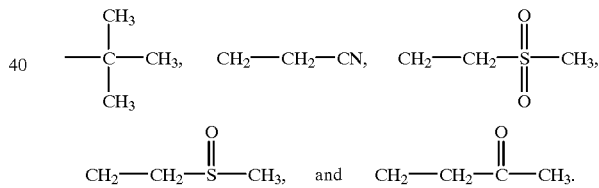

* * * * *